(12) United States Patent
Jackson

(10) Patent No.: US 12,383,746 B2
(45) Date of Patent: *Aug. 12, 2025

(54) SYNCHRONIZATION OF ANTI-TACHYCARDIA PACING IN AN EXTRA-CARDIOVASCULAR IMPLANTABLE SYSTEM

(71) Applicant: Medtronic, Inc., Minneapolis, MN (US)

(72) Inventor: Troy E. Jackson, Rogers, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/464,189

(22) Filed: Sep. 8, 2023

(65) Prior Publication Data

US 2024/0042212 A1 Feb. 8, 2024

Related U.S. Application Data

(63) Continuation of application No. 17/323,008, filed on May 18, 2021, now Pat. No. 11,752,344, which is a
(Continued)

(51) Int. Cl.
*A61N 1/362* (2006.01)
*A61B 5/00* (2006.01)
(Continued)

(52) U.S. Cl.
CPC ............ *A61N 1/3621* (2013.01); *A61B 5/363* (2021.01); *A61B 5/4836* (2013.01);
(Continued)

(58) Field of Classification Search
CPC .... A61B 5/363; A61B 5/4836; A61N 1/0504; A61N 1/0563; A61N 1/3621;
(Continued)

(56) References Cited

U.S. PATENT DOCUMENTS 4,967,746 A 11/1990 Vandegriff
5,181,511 A 1/1993 Nickolls et al.
(Continued)

FOREIGN PATENT DOCUMENTS

CN 1867376 A 11/2006

OTHER PUBLICATIONS

Uldry et al., "Optimization of Antitachycardia Pacing Protocols Applied to Atrial Fibrillation: Insights from a Biophysical Model", at the Proceedings of the 31st Annual International Conference of the IEEE Embs Minneapolis, Minnesota, USA, Sep. 2-6, 2009, 4 pages.
(Continued)

*Primary Examiner* — George Manuel

(57) ABSTRACT

An extra-cardiovascular implantable cardioverter defibrillator (ICD) system receives a cardiac electrical signal by an electrical sensing circuit via an extra-cardiovascular sensing electrode vector and senses cardiac events from the cardiac electrical signal. The ICD system detects tachycardia from the cardiac electrical signal and determines a tachycardia cycle length from the cardiac electrical signal. The ICD system determines an ATP interval based on the tachycardia cycle length and sets an extended ATP interval that is longer than the ATP interval. The ICD delivers ATP pulses to a patient's heart via an extra-cardiovascular pacing electrode vector different than the sensing electrode vector. The ATP pulses include a leading ATP pulse delivered at the extended ATP interval after a cardiac event is sensed from the cardiac electrical signal and a second ATP pulse delivered at the ATP interval following the leading ATP pulse.

21 Claims, 11 Drawing Sheets

Related U.S. Application Data continuation of application No. 15/071,231, filed on Mar. 16, 2016, now Pat. No. 11,027,132.

(51) Int. Cl.
   *A61B 5/363* (2021.01)
   *A61N 1/365* (2006.01)
   *A61N 1/39* (2006.01)
   *A61N 1/05* (2006.01)

(52) U.S. Cl.
   CPC ....... *A61N 1/36514* (2013.01); *A61N 1/3956* (2013.01); *A61N 1/3962* (2013.01); *A61N 1/3987* (2013.01); *A61N 1/0504* (2013.01); *A61N 1/0563* (2013.01); *A61N 1/3622* (2013.01)

(58) Field of Classification Search
   CPC .............. A61N 1/3622; A61N 1/36514; A61N 1/3956; A61N 1/3962; A61N 1/3987; A61N 1/362; A61N 1/39; A51B 5/00
   See application file for complete search history.

(56) References Cited

U.S. PATENT DOCUMENTS

| | | | |
|---|---|---|---|
| 5,331,966 | A | 7/1994 | Bennett et al. |
| 5,339,820 | A | 8/1994 | Henry et al. |
| 5,458,619 | A | 10/1995 | Olson |
| 5,545,186 | A | 8/1996 | Olson et al. |
| 5,755,739 | A | 5/1998 | Sun |
| 6,167,308 | A | 12/2000 | DeGroot |
| 6,654,639 | B1 | 11/2003 | Lu |
| 6,885,890 | B2 | 4/2005 | Spinelli et al. |
| 6,952,610 | B2 | 10/2005 | Ostroff et al. |
| 7,146,214 | B2 | 12/2006 | Struble |
| 7,260,433 | B1 | 8/2007 | Falkenberg et al. |
| 7,277,755 | B1 | 10/2007 | Falkenberg et al. |
| 7,383,091 | B1 | 6/2008 | Chitre |
| 7,386,342 | B1 | 6/2008 | Falkenberg et al. |
| 7,502,645 | B2 | 3/2009 | Ostroff et al. |
| 7,567,835 | B2 | 7/2009 | Gunderson |
| 7,684,862 | B2 | 3/2010 | Belk et al. |
| 7,761,150 | B2 | 7/2010 | Ghanem et al. |
| 7,761,153 | B2 | 7/2010 | Belk et al. |
| 7,761,155 | B2 | 7/2010 | Belk et al. |
| 7,792,578 | B2 | 9/2010 | Belk et al. |
| 7,792,579 | B2 | 9/2010 | Belk et al. |
| 7,813,798 | B2 | 10/2010 | Bornzin |
| 7,844,331 | B2 | 11/2010 | Li et al. |
| 7,957,801 | B2 | 6/2011 | Oosterhoff et al. |
| 8,121,680 | B2 | 2/2012 | Falkenberg et al. |
| 8,170,669 | B2 | 5/2012 | Li et al. |
| 8,600,500 | B1 | 12/2013 | Rosenberg |
| 8,706,221 | B2 | 4/2014 | Belk et al. |
| 8,706,224 | B1 | 4/2014 | Bornzin et al. |
| 9,468,392 | B2 | 10/2016 | Jackson |
| 9,468,766 | B2 | 10/2016 | Sheldon et al. |
| 9,724,519 | B2 | 8/2017 | Demmer et al. |
| 10,675,478 | B2 | 6/2020 | Marshall et al. |
| 11,027,132 | B2 | 6/2021 | Jackson |
| 2005/0021095 | A1 | 1/2005 | Rueter et al. |
| 2006/0217621 | A1* | 9/2006 | Kim ................... A61N 1/39622 600/509 |
| 2006/0247698 | A1 | 11/2006 | Burnes et al. |
| 2007/0173895 | A1 | 7/2007 | Reichenbach |
| 2007/0191897 | A1 | 8/2007 | Belk et al. |
| 2008/0114411 | A1 | 5/2008 | Lian et al. |
| 2009/0005828 | A1 | 1/2009 | Levine |
| 2009/0099616 | A1 | 4/2009 | Li et al. |
| 2010/0228309 | A1 | 9/2010 | Belk et al. |
| 2011/0319952 | A1 | 12/2011 | Virag et al. |
| 2012/0191154 | A1 | 7/2012 | Ryu et al. |
| 2012/0316613 | A1 | 12/2012 | Keefe et al. |
| 2014/0330327 | A1 | 11/2014 | Thompson-Nauman et al. |
| 2015/0290467 | A1 | 10/2015 | Ludwig |
| 2015/0297905 | A1 | 10/2015 | Greenhut et al. |
| 2015/0306375 | A1 | 10/2015 | Marshall et al. |
| 2015/0306410 | A1 | 10/2015 | Marshall et al. |
| 2015/0360041 | A1 | 12/2015 | Stahmann et al. |
| 2016/0030743 | A1 | 2/2016 | Kaiser |
| 2016/0051821 | A1 | 2/2016 | Sambelashvili et al. |
| 2016/0158567 | A1 | 6/2016 | Marshall et al. |
| 2016/0228026 | A1 | 8/2016 | Jackson et al. |
| 2016/0235315 | A1 | 8/2016 | Sarkar et al. |
| 2017/0312534 | A1 | 11/2017 | Cao et al. |
| 2017/0354827 | A1 | 12/2017 | Zhang et al. |
| 2019/0083800 | A1 | 3/2019 | Yang et al. |
| 2019/0134404 | A1 | 5/2019 | Sheldon et al. |

OTHER PUBLICATIONS

Li Xiaoqing, "Effect of Right Ventricular Electrode Position on Clinical Outcomes and the Occurrence of Ventricular Tachycardia in Patients with Cardiac Resynchronization Pacing Defibrillators", in the Chinese Journal of Cardiac Pacing and Electrophysiology, vol. 28 No. 1, Feb. 25, 2014, 1 page.

(PCT/US2017/020413) PCT Notification of Transmittal of the International Search Report and the Written Opinion of the International Searching Authority, Mailed May 22, 2017, 12 pages.

\* cited by examiner

SYNCHRONIZATION OF ANTI-TACHYCARDIA PACING IN AN EXTRA-CARDIOVASCULAR IMPLANTABLE SYSTEM

REFERENCE TO RELATED APPLICATIONS

This application is a Continuation of U.S. patent application Ser. No. 17/323,008, filed May 18, 2021, which is a Continuation of U.S. Pat. No. 11,027,132, filed on Mar. 16, 2016, the entire contents of which is incorporated herein by reference.

TECHNICAL FIELD

The disclosure relates generally to implantable medical devices and, in particular, to a system, device and method for delivering anti-tachycardia pacing pulses using extra-cardiovascular electrodes.

BACKGROUND

A variety of implantable medical devices (IMDs) for delivering a therapy, monitoring a physiological condition of a patient or a combination thereof have been clinically implanted or proposed for clinical implantation in patients. Some IMDs may employ one or more elongated electrical leads carrying stimulation electrodes, sense electrodes, and/or other sensors. IMDs may deliver therapy to or monitor conditions of a variety of organs, nerves, muscle or tissue, such as the heart, brain, stomach, spinal cord, pelvic floor, or the like. Implantable medical leads may be configured to position electrodes or other sensors at desired locations for delivery of electrical stimulation or sensing of physiological conditions. For example, electrodes or sensors may be carried along a distal portion of a lead that is extended subcutaneously, submuscularly, or transvenously. A proximal portion of the lead may be coupled to an implantable medical device housing, which contains circuitry such as signal generation circuitry and/or sensing circuitry.

Some IMDs, such as cardiac pacemakers or implantable cardioverter defibrillators (ICDs), provide therapeutic electrical stimulation to the heart of the patient via electrodes carried by one or more implantable leads and/or the housing of the pacemaker or ICD. The leads may be transvenous, e.g., advanced into the heart through one or more veins to position endocardial electrodes in intimate contact with the heart tissue. Other leads may be non-transvenous leads implanted outside the heart, e.g., implanted epicardially, pericardially, or subcutaneously. The electrodes are used to deliver electrical pulses to the heart to address abnormal cardiac rhythms.

IMDs capable of delivering electrical pulses for treating abnormal cardiac rhythms typically sense signals representative of intrinsic depolarizations of the heart and analyze the sensed signals to identify the abnormal rhythms. Upon detection of an abnormal rhythm, the device may deliver an appropriate electrical stimulation therapy to restore a more normal rhythm. For example, a pacemaker or ICD may deliver pacing pulses to the heart upon detecting bradycardia or tachycardia using endocardial or epicardial electrodes. An ICD may deliver high voltage cardioversion or defibrillation shocks to the heart upon detecting fast ventricular tachycardia or fibrillation using electrodes carried by transvenous leads or non-transvenous leads.

SUMMARY

In general, the disclosure is directed to techniques for delivering extra-cardiovascular anti-tachycardia pacing (ATP) pulses by an implantable medical device. An ICD operating according to the techniques disclosed herein sets an extended leading ATP interval for controlling the time of the leading pulse of a sequence of ATP pulses relative to a cardiac event sensed from a sensing electrode vector. The ATP pulses are delivered using an extra-cardiovascular pacing electrode vector.

In one example, the disclosure provides an extra-cardiovascular implantable cardioverter defibrillator system including an electrical sensing circuit, a therapy delivery circuit and a control circuit. The sensing circuit is configured to receive a cardiac electrical signal via an extra-cardiovascular sensing electrode vector and sense cardiac events from the cardiac electrical signal. The therapy delivery circuit is configured to deliver anti-tachycardia pacing pulses to a patient's heart via an extra-cardiovascular pacing electrode vector different than the extra-cardiovascular sensing electrode vector. The control circuit is coupled to the electrical sensing circuit and the therapy delivery circuit and is configured to detect tachycardia from the cardiac electrical signal, determine a tachycardia cycle length, determine an ATP interval based on the tachycardia cycle length, set an extended ATP interval that is longer than the ATP interval, and control the therapy delivery circuit to deliver a sequence of ATP pulses including a leading ATP pulse delivered at the extended ATP interval after a cardiac event sensed by the electrical sensing circuit and a second ATP pulse delivered at the ATP interval following the leading ATP pulse.

In another example, the disclosure provides a method performed by an extra-cardiovascular ICD system including receiving a cardiac electrical signal by an electrical sensing circuit via an extra-cardiovascular sensing electrode vector, sensing cardiac events from the cardiac electrical signal, and detecting tachycardia from the cardiac electrical signal. The method further includes determining a tachycardia cycle length from the cardiac electrical signal, determining an ATP interval based on the tachycardia cycle length, setting an extended ATP interval that is longer than the ATP interval and delivering ATP pulses to a patient's heart via an extra-cardiovascular pacing electrode vector different than the extra-cardiovascular sensing electrode vector. The ATP pulses include a leading ATP pulse delivered at the extended ATP interval after a cardiac event is sensed by the sensing circuit from the cardiac electrical signal and a second ATP pulse delivered at the ATP interval following the leading ATP pulse.

In another example, the disclosure provides a non-transitory, computer-readable storage medium comprising a set of instructions which, when executed by a control circuit of an extra-cardiovascular implantable cardioverter defibrillator system, cause the system to receive a cardiac electrical signal by an electrical sensing circuit via an extra-cardiovascular sensing electrode vector, sense cardiac events from the cardiac electrical signal, detect tachycardia from the cardiac electrical signal, determine a tachycardia cycle length from the cardiac electrical signal, determine an ATP interval based on the tachycardia cycle length, set an extended ATP interval that is longer than the ATP interval and deliver ATP pulses to a patient's heart via an extra-cardiovascular pacing electrode vector different than the extra-cardiovascular sensing electrode vector. The ATP pulses include a leading ATP pulse delivered at the extended ATP interval after a cardiac event is sensed by the sensing circuit from the cardiac electrical signal and a second ATP pulse delivered at the ATP interval following the leading ATP pulse.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

In general, this disclosure describes techniques for delivering ATP using implanted, extra-cardiovascular electrodes. As used herein, the term "extra-cardiovascular" refers to a position outside the blood vessels, heart, and pericardium surrounding the heart of a patient. Implantable electrodes carried by extra-cardiovascular leads may be positioned extra-thoracically (outside the ribcage and sternum) or intra-thoracically (beneath the ribcage or sternum) but generally not in intimate contact with myocardial tissue. The techniques disclosed herein provide a method for controlling the timing of the leading pulse of an ATP sequence to promote a high likelihood of capturing the myocardium outside of the physiological refractory period of the myocardium at an effective stimulation site.

Figure 1A:
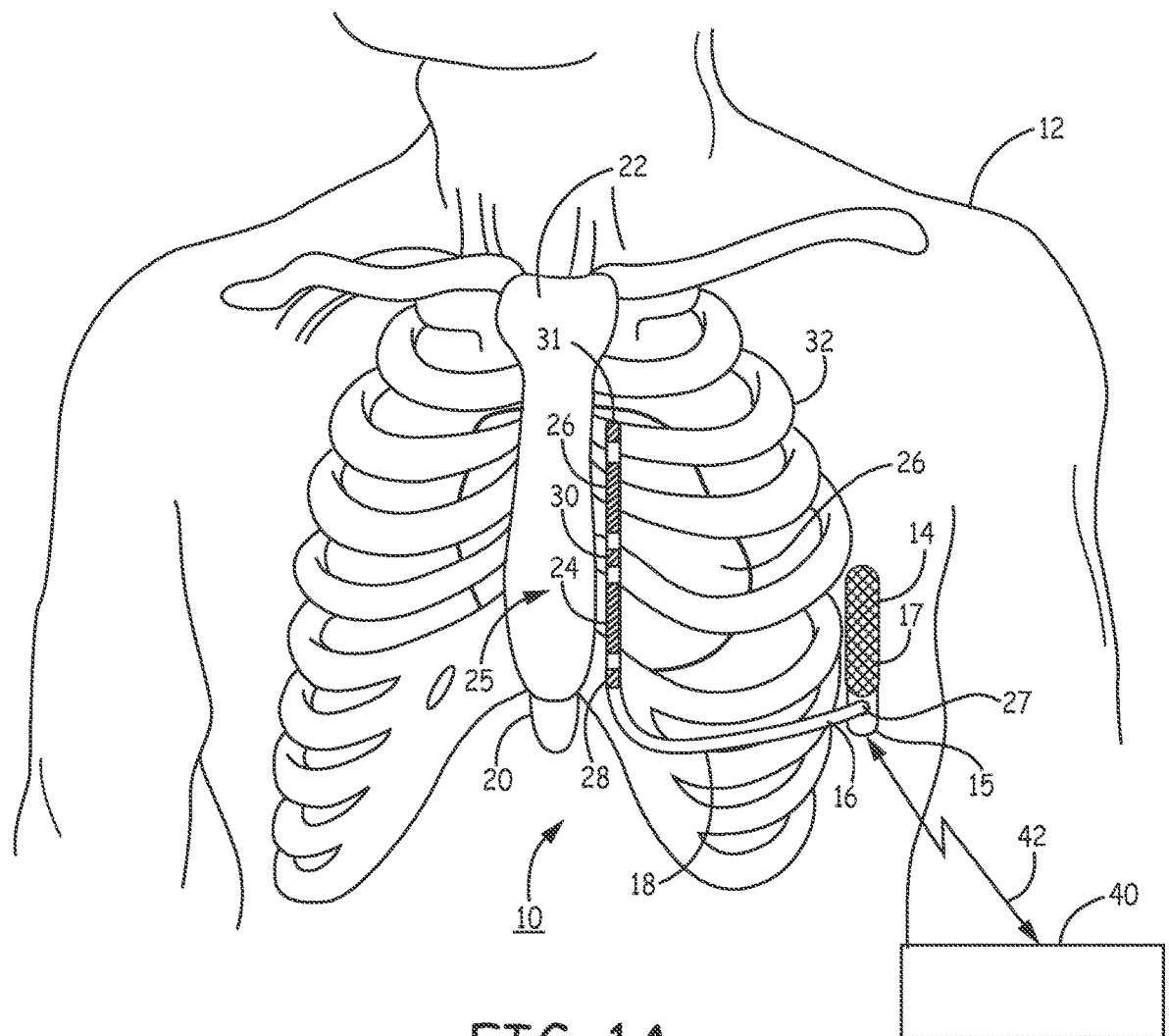
FIGS. 1A and 1B are conceptual diagrams of an extra-cardiovascular ICD system according to one example.
Figure 1B:
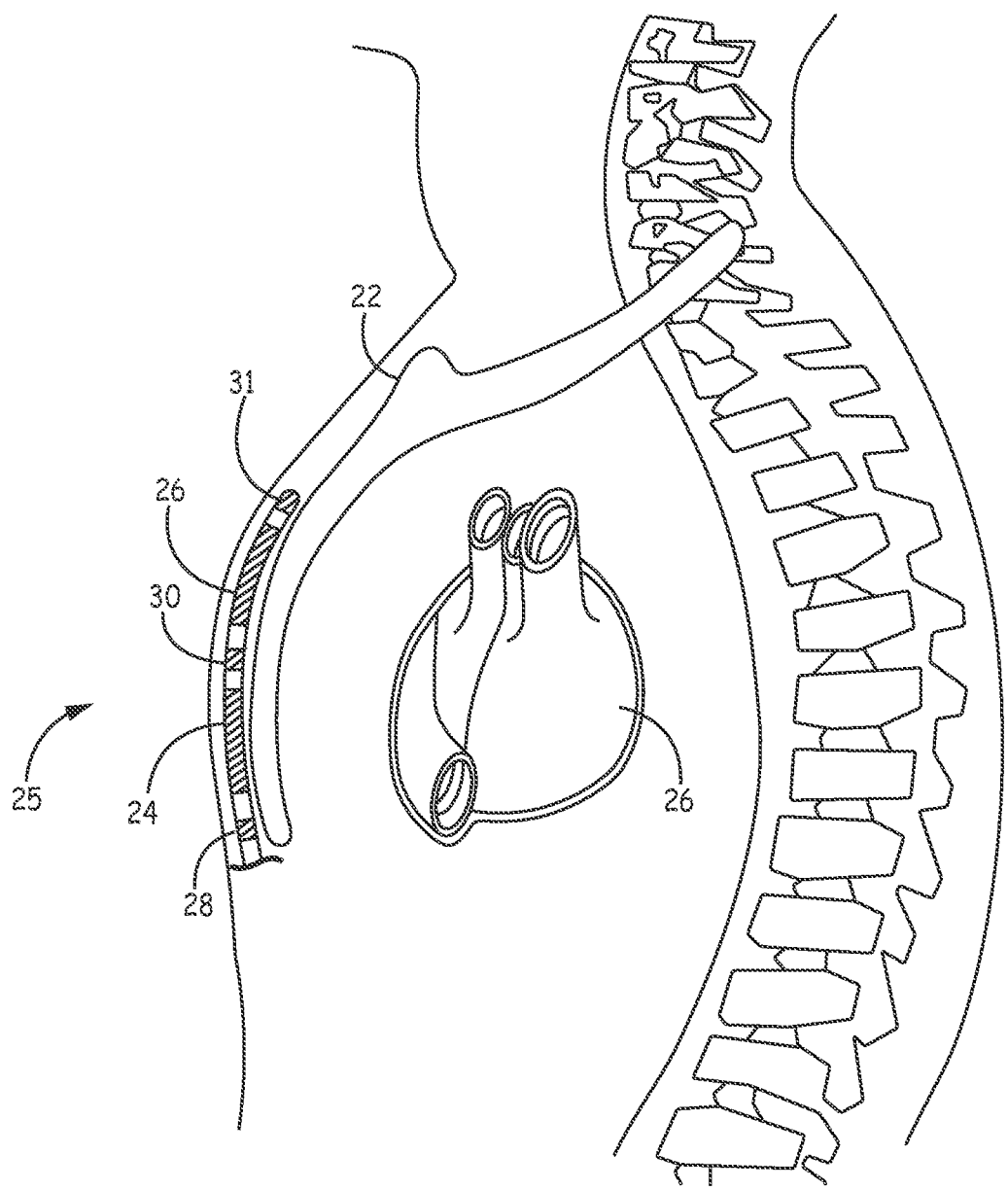

FIGS. 1A and 1B are conceptual diagrams of an extra-cardiovascular ICD system 10 according to one example. FIG. 1A is a front view of ICD system 10 implanted within patient 12. FIG. 1B is a side view of ICD system 10 implanted within patient 12. ICD system 10 includes an ICD 14 connected to an extra-cardiovascular electrical stimulation and sensing lead 16. FIGS. 1A and 1B are described in the context of an ICD system 10 capable of providing defibrillation and/or cardioversion shocks and pacing pulses.

ICD 14 includes a housing 15 that forms a hermetic seal that protects internal components of ICD 14. The housing 15 of ICD 14 may be formed of a conductive material, such as titanium or titanium alloy. The housing 15 may function as a housing electrode (sometimes referred to as a can electrode). In examples described herein, housing 15 may be used as an active can electrode for use in delivering cardioversion/defibrillation (CV/DF) shocks or other high voltage pulses delivered using a high voltage therapy circuit. In other examples, housing 15 may be available for use in delivering unipolar, low voltage cardiac pacing pulses in conjunction with lead-based cathode electrodes. In other instances, the housing 15 of ICD 14 may include a plurality of electrodes on an outer portion of the housing. The outer portion(s) of the housing 15 functioning as an electrode(s) may be coated with a material, such as titanium nitride.

ICD 14 includes a connector assembly 17 (also referred to as a connector block or header) that includes electrical feedthroughs crossing housing 15 to provide electrical connections between conductors extending within the lead body 18 of lead 16 and electronic components included within the housing 15 of ICD 14. As will be described in further detail herein, housing 15 may house one or more processors, memories, transceivers, sensors, electrical sensing circuitry, therapy delivery circuitry, power sources and other components for sensing cardiac electrical signals, detecting a heart rhythm, and controlling and delivering electrical stimulation pulses to treat an abnormal heart rhythm.

Lead 16 includes an elongated lead body 18 having a proximal end 27 that includes a lead connector (not shown) configured to be connected to ICD connector assembly 17 and a distal portion 25 that includes one or more electrodes. In the example illustrated in FIGS. 1A and 1B, the distal portion 25 of lead 16 includes defibrillation electrodes 24 and 26 and pace/sense electrodes 28, 30 and 31. In some cases, defibrillation electrodes 24 and 26 may together form a defibrillation electrode in that they may be configured to be activated concurrently. Alternatively, defibrillation electrodes 24 and 26 may form separate defibrillation electrodes in which case each of the electrodes 24 and 26 may be activated independently. In some instances, defibrillation electrodes 24 and 26 are coupled to electrically isolated conductors, and ICD 14 may include switching mechanisms to allow electrodes 24 and 26 to be utilized as a single defibrillation electrode (e.g., activated concurrently to form a common cathode or anode) or as separate defibrillation electrodes, (e.g., activated individually, one as a cathode and one as an anode or activated one at a time, one as an anode or cathode and the other remaining inactive with housing 15 as an active electrode).

Electrodes 24 and 26 (and in some examples housing 15) are referred to herein as defibrillation electrodes because they are utilized, individually or collectively, for delivering high voltage stimulation therapy (e.g., cardioversion or defibrillation shocks). Electrodes 24 and 26 may be elongated coil electrodes and generally have a relatively high surface area for delivering high voltage electrical stimulation pulses compared to low voltage pacing and sensing electrodes 28, 30 and 31. However, electrodes 24 and 26 and housing 15 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 24 and 26 for use in only high voltage cardioversion/defibrillation shock therapy applications. As described herein, electrodes 24 and 26 may be used in a pacing electrode vector for delivering extra-cardiovascular pacing pulses such as ATP pulses and/or in a sensing vector used to sense cardiac electrical signals and detect ventricular tachycardia (VT) and ventricular fibrillation (VF).

Electrodes 28, 30 and 31 are relatively smaller surface area electrodes for delivering low voltage pacing pulses and for sensing cardiac electrical signals. Electrodes 28, 30 and 31 are referred to as pace/sense electrodes because they are generally configured for use in low voltage applications, e.g., used as either a cathode or anode for delivery of pacing pulses and/or sensing of cardiac electrical signals. In some instances, electrodes 28, 30 and 31 may provide only pacing functionality, only sensing functionality or both.

In the example illustrated in FIGS. 1A and 1B, electrode 28 is located proximal to defibrillation electrode 24, and electrode 30 is located between defibrillation electrodes 24 and 26. A third pace/sense electrode 31 may be located distal to defibrillation electrode 26. In other examples, none, one or more pace/sense electrodes may be located proximal to defibrillation electrode 24, none, one or more pace/sense electrodes may be located between defibrillation electrodes 24 and 26, and/or none, one or more pace/sense electrodes may be located distal to defibrillation electrode 26.

Electrodes 28 and 30 are illustrated as ring electrodes, and electrode 31 is illustrated as a hemispherical tip electrode in the example of FIGS. 1A and 1B. However, electrodes 28, 30 and 31 may comprise any of a number of different types of electrodes, including ring electrodes, short coil electrodes, hemispherical electrodes, directional electrodes, segmented electrodes, or the like, and may be positioned at any position along the distal portion 25 of lead 16. Further, electrodes 28, 30 and 31 may be of similar type, shape, size and material or may differ from each other.

Lead 16 extends subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 bends or turns and extends superior subcutaneously or submuscularly over the ribcage and/or sternum, substantially parallel to sternum 22. Although illustrated in FIGS. 1A and 1B as being offset laterally from and extending substantially parallel to sternum 22, lead 16 may be implanted at other locations, such as over sternum 22, offset to the right or left of sternum 22, angled laterally from sternum 22 toward the left or the right, or the like. Alternatively, lead 16 may be placed along other subcutaneous or submuscular paths. The path of lead 16 may depend on the location of ICD 14, the arrangement and position of electrodes carried by the lead distal portion 25, and/or other factors.

Electrical conductors (not illustrated) extend through one or more lumens of the elongated lead body 18 of lead 16 from the lead connector at the proximal lead end 27 to electrodes 24, 26, 28, 30 and 31 located along the distal portion 25 of the lead body 18. Lead body 18 may be tubular or cylindrical in shape. In other examples, the distal portion 25 (or all of) the elongated lead body 18 may have a flat, ribbon or paddle shape. The lead body 18 of lead 16 may be formed from a non-conductive material, including silicone, polyurethane, fluoropolymers, mixtures thereof, and other appropriate materials, and shaped to form one or more lumens within which the one or more conductors extend. However, the techniques disclosed herein are not limited to such constructions or to any particular lead body design.

The elongated electrical conductors contained within the lead body 18 are each electrically coupled with respective defibrillation electrodes 24 and 26 and pace/sense electrodes 28, 30 and 31. Each of pacing and sensing electrodes 28, 30 and 31 are coupled to respective electrical conductors, which may be separate respective conductors within the lead body. The respective conductors electrically couple the electrodes 24, 26, 28, 30 and 31 to circuitry, such as a therapy circuit and/or a sensing circuit, of ICD 14 via connections in the connector assembly 17, including associated electrical feedthroughs crossing housing 15. The electrical conductors transmit therapy from a therapy circuit within ICD 14 to one or more of defibrillation electrodes 24 and 26 and/or pace/sense electrodes 28, 30 and 31 and transmit sensed electrical signals from one or more of defibrillation electrodes 24 and 26 and/or pace/sense electrodes 28, 30 and 31 to the sensing circuit within ICD 14.

ICD 14 may obtain electrical signals corresponding to electrical activity of heart 26 via a combination of sensing vectors that include combinations of electrodes 28, 30, and/or 31. In some examples, housing 15 of ICD 14 is used in combination with one or more of electrodes 28, 30 and/or 31 in a sensing electrode vector. ICD 14 may even obtain cardiac electrical signals using a sensing vector that includes one or both defibrillation electrodes 24 and/or 26, e.g., between electrodes 24 and 26 or one of electrodes 24 or 26 in combination with one or more of electrodes 28, 30, 31, and/or the housing 15.

ICD 14 analyzes the cardiac electrical signals received from one or more of the sensing vectors to monitor for abnormal rhythms, such as bradycardia, ventricular tachycardia (VT) or ventricular fibrillation (VF). ICD 14 may analyze the heart rate and/or morphology of the cardiac electrical signals to monitor for tachyarrhythmia in accordance with any of a number of tachyarrhythmia detection techniques. One example technique for detecting tachyarrhythmia is described in U.S. Pat. No. 7,761,150 (Ghanem, et al.), incorporated by reference herein in its entirety.

ICD 14 generates and delivers electrical stimulation therapy in response to detecting a tachyarrhythmia (e.g., VT or VF). ICD 14 may deliver ATP in response to VT detection, and in some cases may deliver ATP prior to a CV/DF shock or during high voltage capacitor charging in an attempt to avert the need for delivering a CV/DF shock. ATP may be delivered using an extra-cardiovascular pacing electrode vector selected from any of electrodes 24, 26, 28, 30, 31 and/or housing 15. The pacing electrode vector may be different than the sensing electrode vector. In one example, cardiac electrical signals are sensed between pace/sense electrodes 28 and 30, and ATP pulses are delivered between pace/sense electrode 30 used as a cathode electrode and defibrillation electrode 24 used as a return anode electrode. In other examples, ATP pulses may be delivered between pace/sense electrode 28 and either (or both) defibrillation electrode 24 or 26 or between defibrillation electrode 24 and defibrillation electrode 26. These examples are not intended to be limiting, and it is recognized that other sensing electrode vectors and ATP electrode vectors may be selected according to individual patient need.

The myocardial site that is first captured by an ATP pulse delivered by the selected extra-cardiovascular pacing electrode vector is referred to herein as the "capture site" which is spaced apart from the pacing cathode electrode and the pacing anode electrode that are not in direct contact with the myocardium in an extra-cardiovascular ICD system, such as system 10. A time difference may exist between the time that an R-wave is sensed by the sensing electrode vector and the time that the intrinsic, propagating depolarization associated with the sensed R-wave actually arrives at the capture site. The distance of the extra-cardiovascular electrodes from each other and from the heart can result in a significant time difference between the time the R-wave is sensed by the extra-cardiovascular sensing electrode vector and the time that the myocardial cells at the capture site depolarize and repolarize. If the tissue at the capture site is in physiological refractory when an ATP pulse is delivered, the pulse will not capture the heart.

In order to successfully terminate a detected VT, it is desirable that all ATP pulses capture the myocardium to overdrive pace the heart back into a normal sinus rhythm. In order to overdrive pace the heart, each pacing pulse of the ATP sequence should arrive at the capture site after the physiological refractory period that follows the previous myocardial depolarization and before the next expected intrinsic ventricular depolarization. Accordingly, ATP pulses may be delivered at pacing intervals that are shorter than the detected VT interval but longer than the expected physiological refractory period following a sensed R-wave or the preceding ATP pulse. By capturing the myocardium with the leading ATP pulse at a time interval that is shorter than the detected VT interval, the remaining ATP pulses are more likely to capture the myocardium because they will also be properly timed relative to the myocardial refractory period thereby increasing the likelihood of successfully terminating the VT.

The potential time difference between a sensed R-wave used to control timing of the leading ATP pulse and the time of depolarization at the capture site, however, may result in failed capture by the leading ATP pulse if the capture site is still refractory at the time of pulse delivery. The techniques disclosed herein take into account for this possible time difference between a sensed R-wave and the time of actual depolarization and repolarization at the capture site. Such a time difference may be non-existent or negligible in transvenous ICD systems or any system capable of delivering ATP using endocardial or epicardial electrodes that are in direct or intimate contact with the myocardial tissue.

If ATP does not successfully terminate VT or when VF is detected, ICD 14 may deliver one or more cardioversion or defibrillation (CV/DF) shocks via one or both of defibrillation electrodes 24 and 26 and/or housing 15. ICD 14 may deliver the CV/DF shocks using electrodes 24 and 26 individually or together as a cathode (or anode) and with the housing 15 as an anode (or cathode). ICD 14 may generate and deliver other types of electrical stimulation pulses such as post-shock pacing pulses or bradycardia pacing pulses using a pacing electrode vector that includes one or more of the electrodes 24, 26, 28, 30 and 31 and the housing 15 of ICD 14.

FIGS. 1A and 1B are illustrative in nature and should not be considered limiting of the practice of the techniques disclosed herein. In other examples, lead 16 may include less than three pace/sense electrodes or more than three pace/sense electrodes and/or a single defibrillation electrode or more than two electrically isolated or electrically coupled defibrillation electrodes or electrode segments. The pace/sense electrodes 28, 30 and/or 31 may be located elsewhere along the length of lead 16. For example, lead 16 may include a single pace/sense electrode 30 between defibrillation electrodes 24 and 26 and no pace/sense electrode distal to defibrillation electrode 26 or proximal defibrillation electrode 24. Various example configurations of extra-cardiovascular leads and electrodes and dimensions that may be implemented in conjunction with the extra-cardiovascular pacing techniques disclosed herein are described in U.S. Publication No. 2015/0306375 (Marshall, et al.) and U.S. Publication No. 2015/0306410 (Marshall, et al.), both of which are incorporated herein by reference in their entirety.

ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferior from the manubrium to the desired location subcutaneously or submuscularly. In yet another example, ICD 14 may be placed abdominally. Lead 16 may be implanted in other extra-cardiovascular locations as well. For instance, as described with respect to FIGS. 2A-2C, the distal portion 25 of lead 16 may be implanted underneath the sternum/ribcage in the substernal space.

An external device 40 is shown in telemetric communication with ICD 14 by a communication link 42. External device 40 may include a processor, display, user interface, telemetry unit and other components for communicating with ICD 14 for transmitting and receiving data via communication link 42. Communication link 42 may be established between ICD 14 and external device 40 using a radio frequency (RF) link such as BLUETOOTH®, Wi-Fi, or Medical Implant Communication Service (MICS) or other RF or communication frequency bandwidth.

External device 40 may be embodied as a programmer used in a hospital, clinic or physician's office to retrieve data from ICD 14 and to program operating parameters and algorithms in ICD 14 for controlling ICD functions. External device 40 may be used to program cardiac rhythm detection parameters and therapy control parameters used by ICD 14. Control parameters used to generate and deliver ATP according to techniques disclosed herein may be programmed into ICD 14 using external device 40.

Data stored or acquired by ICD 14, including physiological signals or associated data derived therefrom, results of device diagnostics, and histories of detected rhythm episodes and delivered therapies, may be retrieved from ICD 14 by external device 40 following an interrogation command. External device 40 may alternatively be embodied as a home monitor or hand held device.

Figure 2A:
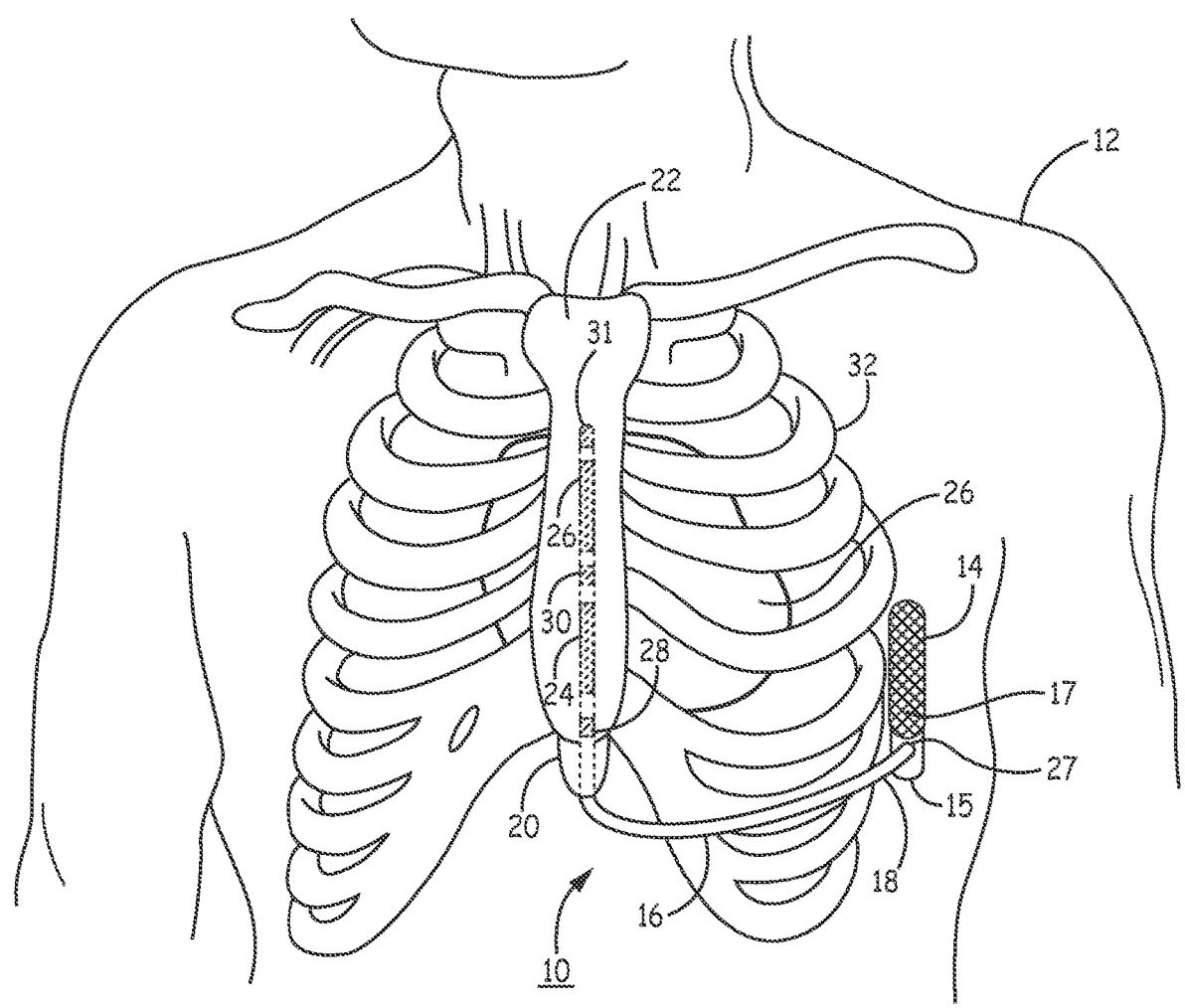
FIGS. 2A-2C are conceptual diagrams of patient 12 implanted with ICD system 10 in a different implant configuration than the arrangement shown in FIGS. 1A-1B.
Figure 2B:
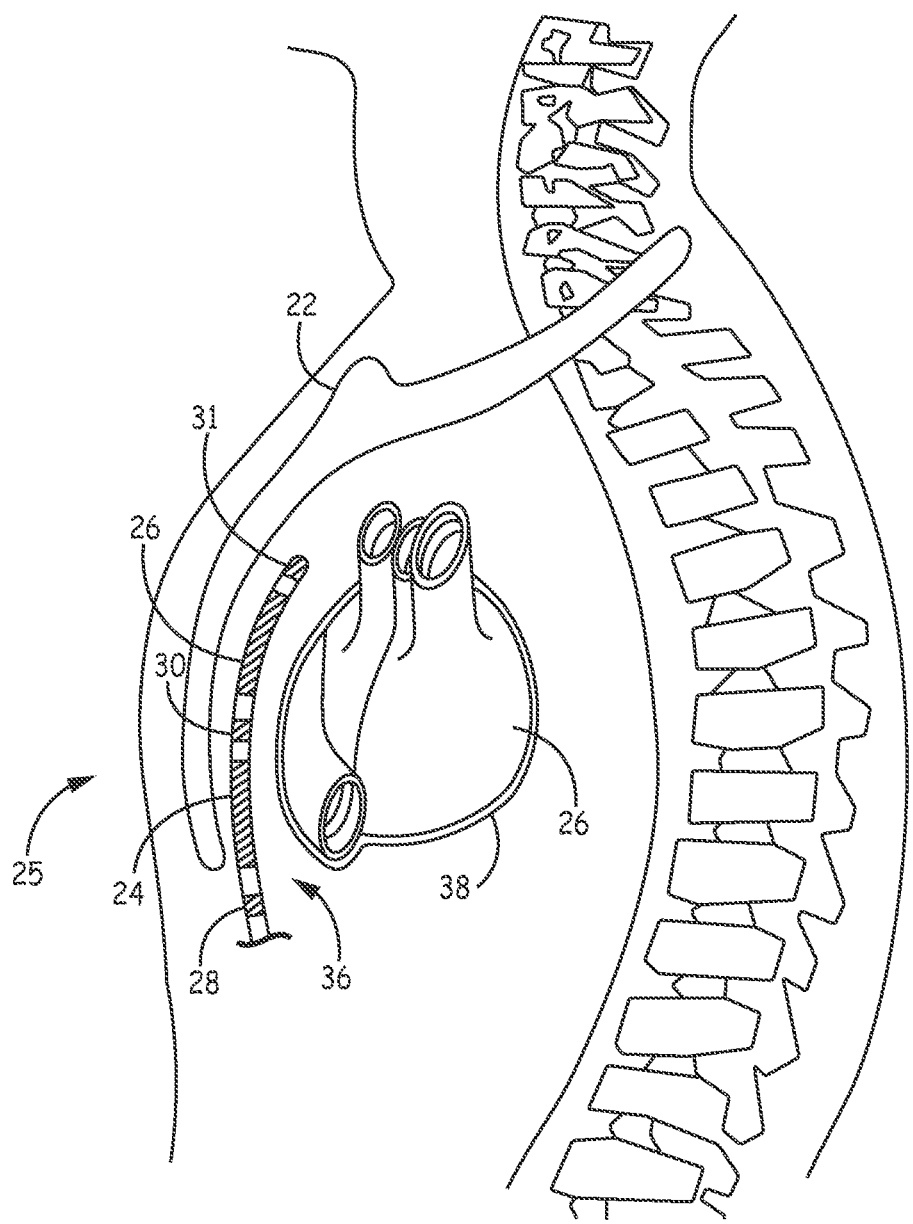
Figure 2C:
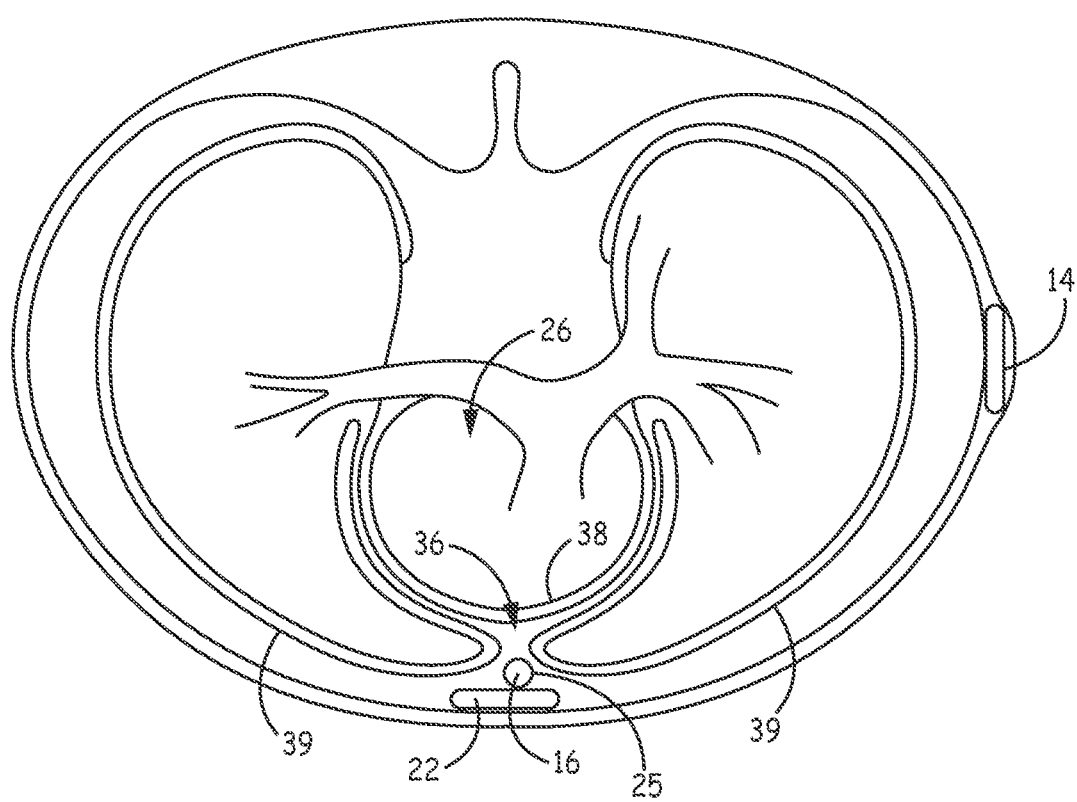

FIGS. 2A-2C are conceptual diagrams of patient 12 implanted with extra-cardiovascular ICD system 10 in a different implant configuration than the arrangement shown in FIGS. 1A-1B. FIG. 2A is a front view of patient 12 implanted with ICD system 10. FIG. 2B is a side view of patient 12 implanted with ICD system 10. FIG. 2C is a transverse view of patient 12 implanted with ICD system 10. In this arrangement, lead 16 of system 10 is implanted at least partially underneath sternum 22 of patient 12. Lead 16 extends subcutaneously or submuscularly from ICD 14 toward xiphoid process 20 and at a location near xiphoid process 20 bends or turns and extends superiorly within anterior mediastinum 36 in a substernal position.

Anterior mediastinum 36 may be viewed as being bounded laterally by pleurae 39, posteriorly by pericardium 38, and anteriorly by sternum 22. In some instances, the anterior wall of anterior mediastinum 36 may also be formed by the transversus thoracis muscle and one or more costal cartilages. Anterior mediastinum 36 includes a quantity of loose connective tissue (such as areolar tissue), adipose tissue, some lymph vessels, lymph glands, substernal musculature, small side branches of the internal thoracic artery or vein, and the thymus gland. In one example, the distal portion 25 of lead 16 extends along the posterior side of sternum 22 substantially within the loose connective tissue and/or substernal musculature of anterior mediastinum 36.

A lead implanted such that the distal portion 25 is substantially within anterior mediastinum 36 may be referred to as a "substernal lead." In the example illustrated in FIGS. 2A-2C, lead 16 is located substantially centered under sternum 22. In other instances, however, lead 16 may be implanted such that it is offset laterally from the center of sternum 22. In some instances, lead 16 may extend laterally such that distal portion 25 of lead 16 is underneath/below the ribcage 32 in addition to or instead of sternum 22. In other examples, the distal portion 25 of lead 16 may be implanted in other extra-cardiovascular, intra-thoracic locations, including the pleural cavity or around the perimeter of and adjacent to but typically not within the pericardium 38 of heart 26. Other implant locations and lead and electrode arrangements that may be used in conjunction with the cardiac pacing techniques described herein are generally disclosed in the above-incorporated patent applications.

Figure 3:
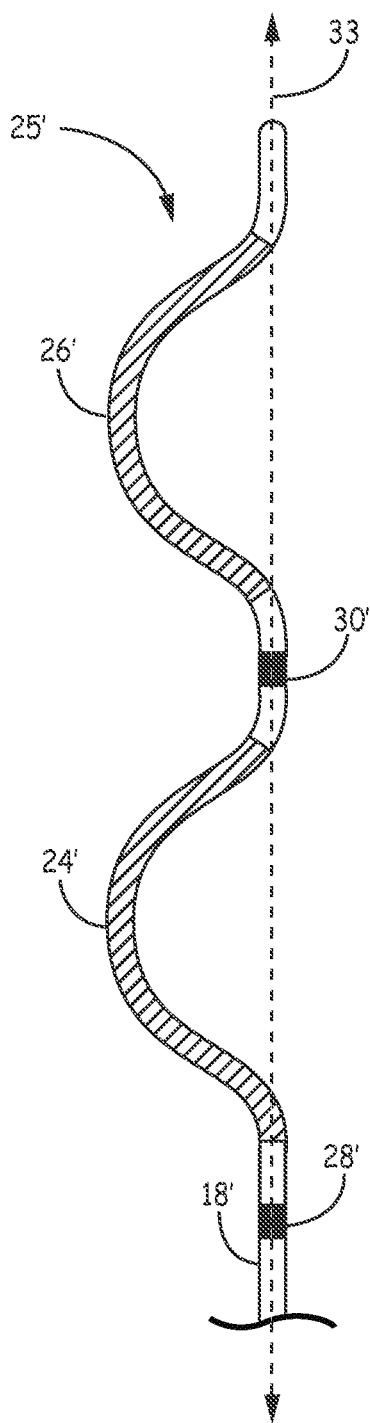
FIG. 3 is a conceptual diagram illustrating a distal portion of another example of the extra-cardiovascular lead of FIGS. 1A-2C.

FIG. 3 is a conceptual diagram illustrating a distal portion 25' of another example of extra-cardiovascular lead 16 of FIGS. 1A-2C having a curving distal portion 25' of lead body 18'. Lead body 18' may be formed having a curving, bending, serpentine, or zig-zagging shape along distal portion 25'. In the example shown, defibrillation electrodes 24' and 26' are carried along curving portions of the lead body 18'. Pace/sense electrode 30' is carried in between defibrillation electrodes 24' and 26'. Pace/sense electrode 28' is carried proximal to the proximal defibrillation electrode 24'. No electrode is provided distal to defibrillation electrode 26' in this example.

As shown in FIG. 3, lead body 18' may be formed having a curving distal portion 25' that includes two "C" shaped curves, which together may resemble the Greek letter epsilon, "ε." Defibrillation electrodes 24' and 26' are each carried by one of the two respective C-shaped portions of the lead body distal portion 25', which extend or curve in the same direction away from a central axis 31 of lead body 18'. In the example shown, pace/sense electrode 28' is proximal to the C-shaped portion carrying electrode 24', and pace/sense electrode 30' is proximal to the C-shaped portion carrying electrode 26'. Pace/sense electrodes 28' and 30' may, in some instances, be approximately aligned with the central axis 31 of the straight, proximal portion of lead body 18' such that mid-points of defibrillation electrodes 24' and 26' are laterally offset from electrodes 28' and 30'. Other examples of extra-cardiovascular leads including one or more defibrillation electrodes and one or more pacing and sensing electrodes carried by curving, serpentine, undulating or zig-zagging distal portion of the lead body that may be implemented with the pacing techniques described herein are generally disclosed in U.S. patent application Ser. No. 14/963,303, incorporated herein by reference in its entirety.

Figure 4:
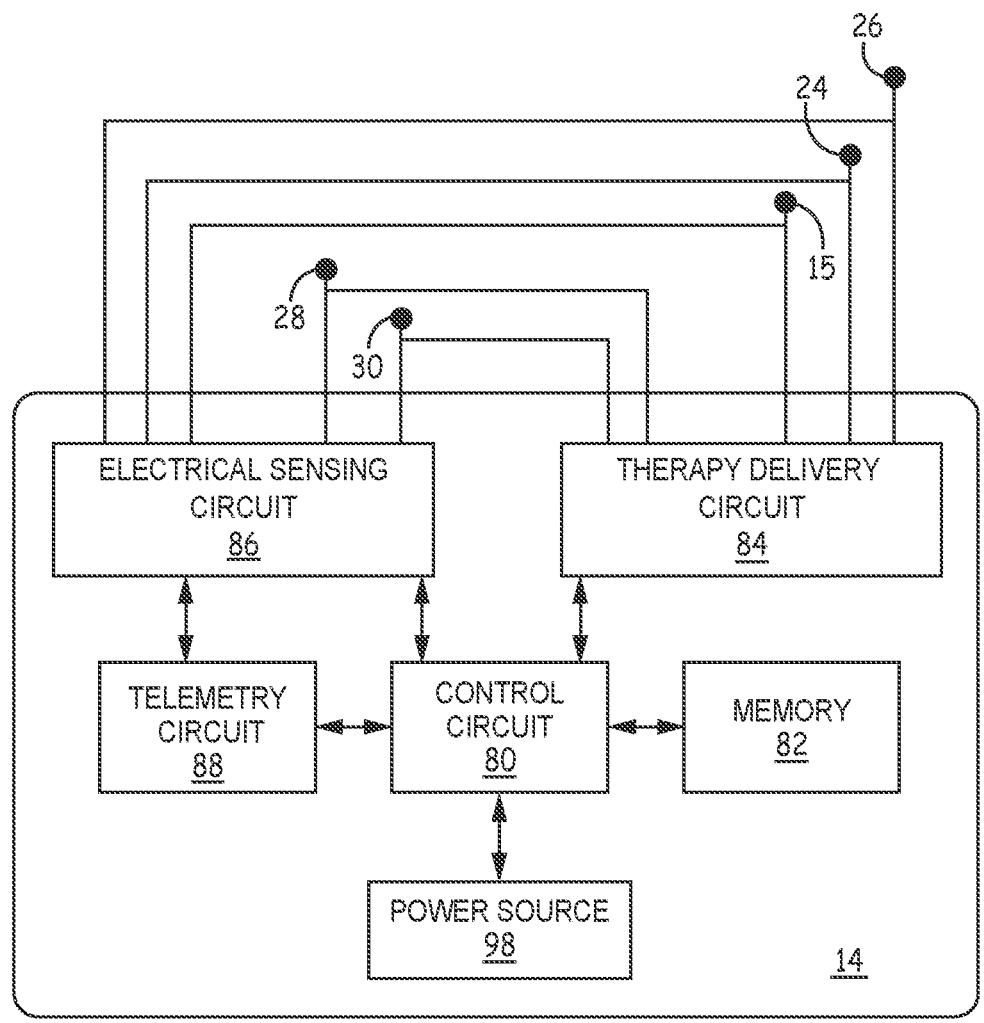
FIG. 4 is a schematic diagram of the ICD of FIGS. 1A-2C according to one example.

FIG. 4 is a schematic diagram of ICD 14 according to one example. The electronic circuitry enclosed within housing 15 (shown schematically as an electrode in FIG. 4) includes software, firmware and hardware that cooperatively monitor one or more cardiac electrical signals, determine when an electrical stimulation therapy is necessary, and deliver therapies as needed according to programmed therapy delivery algorithms and control parameters. The software, firmware and hardware are configured to detect and discriminate VT and VF for determining when ATP or CV/DF shocks are required. ICD 14 is coupled to an extra-cardiovascular lead, such as lead 16 carrying extra-cardiovascular electrodes 24, 26, 28, 30 and 31, for delivering electrical stimulation pulses to the patient's heart and for sensing cardiac electrical signals.

ICD 14 includes a control circuit 80, memory 82, therapy delivery circuit 84, electrical sensing circuit 86, and telemetry circuit 88. A power source 98 provides power to the circuitry of ICD 14, including each of the components 80, 82, 84, 86, and 88 as needed. Power source 98 may include one or more energy storage devices, such as one or more rechargeable or non-rechargeable batteries. The connections between power source 98 and each of the other components 80, 82, 84, 86 and 88 are to be understood from the general block diagram of FIG. 4, but are not shown for the sake of clarity. For example, power source 98 may be coupled to a low voltage charging circuit and to a high voltage charging circuit included in therapy delivery circuit 84 for charging low voltage and high voltage capacitors, respectively, included in therapy delivery circuit 84 for producing respective low voltage pacing pulses, such as bradycardia pacing, post-shock pacing or ATP pulses, or for producing high voltage pulses, such as CV/DF shock pulses. In some examples, high voltage capacitors are charged and utilized for delivering ATP instead of low voltage capacitors.

The functional blocks shown in FIG. 4 represent functionality included in ICD 14 and may include any discrete and/or integrated electronic circuit components that implement analog and/or digital circuits capable of producing the functions attributed to ICD 14 herein. The various components may include an application specific integrated circuit (ASIC), an electronic circuit, a processor (shared, dedicated, or group) and memory that execute one or more software or firmware programs, a combinational logic circuit, state machine, or other suitable components that provide the described functionality. The particular form of software, hardware and/or firmware employed to implement the functionality disclosed herein will be determined primarily by the particular system architecture employed in the device and by the particular detection and therapy delivery methodologies employed by the ICD 14. Providing software, hardware, and/or firmware to accomplish the described functionality in the context of any modern ICD system, given the disclosure herein, is within the abilities of one of skill in the art.

Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control circuit 80 or other ICD components to perform various functions attributed to ICD 14 or those ICD components. The non-transitory computer-readable media storing the instructions may include any of the media listed above.

The functions attributed to ICD 14 herein may be embodied as one or more integrated circuits. Depiction of different features as components (e.g., circuits) is intended to highlight different functional aspects and does not necessarily imply that such components (e.g., circuits or modules) must be realized by separate hardware or software components. Rather, functionality associated with one or more components may be performed by separate hardware, firmware or software components, or integrated within common hardware, firmware or software components. For example, ATP delivery operations may be performed by therapy delivery circuit 84 under the control of control circuit 80 and may include operations implemented in a processor executing instructions stored in memory 82 and control signals such as timing and pacing pulse amplitude signals sent from control circuit 80 to therapy delivery circuit 84.

Control circuit 80 communicates, e.g., via a data bus, with therapy delivery circuit 84 and electrical sensing circuit 86 for sensing cardiac electrical activity, detecting cardiac rhythms, and controlling delivery of cardiac electrical stimulation therapies in response to sensed cardiac signals. Therapy delivery circuit 84 and electrical sensing circuit 86 are electrically coupled to electrodes 24, 26, 28, and 30 (and 31 if present) carried by lead 16 (e.g., as shown in FIG. 3) and the housing 15, which may function as a common or ground electrode or as an active can electrode for delivering CV/DF shock pulses or ATP pulses.

Electrical sensing circuit 86 may be selectively coupled to electrodes 28, 30 and/or housing 15 in order to monitor electrical activity of the patient's heart. Electrical sensing circuit 86 may additionally be selectively coupled to defibrillation electrodes 24 and/or 26 for use in a sensing electrode vector. Sensing circuit 86 is enabled to selectively monitor one or more sensing vectors at a time selected from the available electrodes 24, 26, 28, 30 and housing 15. For example, sensing circuit 86 may include switching circuitry for selecting which of electrodes 24, 26, 28, 30 and housing 15 are coupled to sense amplifiers or other cardiac event detection circuitry included in sensing circuit 86. Switching circuitry may include a switch array, switch matrix, multiplexer, or any other type of switching device suitable to selectively couple components of sensing circuit 86 to selected electrodes. In some instances, control circuit 80 may control the switching circuitry to selectively couple sensing circuit 86 to one or more sense electrode vectors. The cardiac event detection circuitry within electrical sensing circuit 86 may include one or more sense amplifiers, filters, rectifiers, threshold detectors, comparators, analog-to-digital converters (ADCs), or other analog or digital components.

In some examples, electrical sensing circuit 86 includes multiple sensing channels for acquiring cardiac electrical signals from multiple sensing vectors selected from electrodes 24, 26, 28, 30 and housing 15. Each sensing channel may be configured to amplify, filter and rectify the cardiac electrical signal received from selected electrodes coupled to the respective sensing channel to improve the signal quality for sensing cardiac events, e.g., R-waves. For example, each sensing channel may include a pre-filter and amplifier for filtering and amplifying a signal received from a selected pair of electrodes. The resulting raw cardiac electrical signal may be passed from the pre-filter and amplifier to cardiac event detection circuitry for sensing cardiac events from the received cardiac electrical signal. Cardiac event detection circuitry may include a rectifier, post-filter and amplifier, a sense amplifier, comparator, and/or analog-to-digital converter for detecting a cardiac event when the cardiac electrical signal crosses a sensing threshold. The sensing threshold may be set by control circuit 80, based on value stored in memory 82 which may be programmed by a user, and passed from control circuit 80 to sensing circuit 86 via a data bus. Sensing circuit 86 may include an auto-adjusting sense amplifier that compares the cardiac signal to a sensing threshold that decays from a starting value to a minimum sensing floor in some examples.

Upon detecting a cardiac event, electrical sensing circuit 86 may produce a sensed event signal, such as an R-wave sensed event signal, that is passed to control circuit 80. The sensed event signals are used by control circuit 80 for detecting cardiac rhythms and determining a need for therapy. Electrical sensing circuit 86 may also pass a digitized electrocardiogram (ECG) signal to control circuit 80 for morphology analysis performed for detecting and discriminating heart rhythms.

Signals from the selected sensing vector may be passed through a bandpass filter and amplifier, provided to a multiplexer and thereafter converted to multi-bit digital signals by an analog-to-digital converter, all included in sensing circuit 86, for storage in random access memory included in memory 82 under control of a direct memory access circuit via a data/address bus. Control circuit 80 may be a microprocessor based controller that employs digital signal analysis techniques to characterize the digitized signals stored in random access memory of memory 82 to recognize and classify the patient's heart rhythm employing any of numerous signal processing methodologies for analyzing cardiac signals and cardiac event waveforms, e.g., R-waves. One tachyarrhythmia detection system is described in U.S. Pat. No. 5,545,186 (Olson et al.), incorporated herein by reference in its entirety.

Therapy delivery circuit 84 includes charging circuitry, one or more charge storage devices, such as one or more high voltage capacitors and in some examples one or more low voltage capacitors, and switching circuitry that controls when the capacitor(s) are discharged across a selected pacing electrode vector or CV/DF shock vector. Charging of capacitors to a programmed pulse amplitude and discharging of the capacitors for a programmed pulse width may be performed by therapy delivery circuit 84 according to control signals received from control circuit 80. Control circuit 80 may include various timers or counters that control when ATP pulses are delivered.

For example, control circuit 80 may include pacer timing and control circuitry having programmable digital counters set by the microprocessor of the control circuit 80 for controlling the basic time intervals associated with various pacing modes or anti-tachycardia pacing sequences delivered by ICD 14. The microprocessor of control circuit 80 may also set the amplitude, pulse width, polarity or other characteristics of the cardiac pacing pulses, which may be based on programmed values stored in memory 82.

During pacing, escape interval counters within the pacer timing and control circuitry are reset upon sensing of R-waves as indicated by signals from sensing circuit 86. In accordance with the selected mode of pacing, pacing pulses are generated by a pulse output circuit of therapy delivery circuit 84. The pace output circuit is coupled to the desired electrodes via switch matrix for discharging one or more capacitors across the pacing load. The escape interval counters are reset upon generation of pacing pulses, and thereby control the basic timing of cardiac pacing functions, including anti-tachycardia pacing. The durations of the escape intervals are determined by control circuit 80 via a data/address bus. The value of the count present in the escape interval counters when reset by sensed R-waves can be used to measure R-R intervals for detecting the occurrence of a variety of arrhythmias.

Memory 82 includes read-only memory (ROM) in which stored programs controlling the operation of the control circuit 80 reside. Memory 82 may further include random access memory (RAM) configured as a number of recirculating buffers capable of holding a series of measured intervals for analysis by the control circuit 80 for predicting or diagnosing an arrhythmia.

In response to the detection of ventricular tachycardia, anti-tachycardia pacing therapy can be delivered by loading a regimen from the microprocessor included in control circuit 80 into the pacer timing and control circuit according to the type and rate of tachycardia detected. As described below, in accordance with the techniques disclosed herein, the microprocessor or other control circuitry included in control circuit 80 may be programmed or configured to determine a time difference between an R-wave sensed by electrical sensing circuit 86 using a first sensing electrode vector, e.g., between pace/sense electrodes 28 and 30 as shown in FIG. 1, to a fiducial point of an R-wave signal obtained by electrical sensing circuit 86 using a second sensing electrode vector, e.g., between pace/sense electrode 30 and defibrillation electrode 24. The second sensing electrode vector may be the electrode vector used for delivering ATP or at least includes one of the electrodes used to deliver ATP, e.g., between pace/sense electrode 30 used as a cathode electrode and defibrillation electrode 24 used as a return anode electrode.

In response to detecting VT, the microprocessor of control circuit 80 may determine the VT cycle length (e.g., using counters for determining time intervals between consecutive R-wave sensed event signals). Based on the VT cycle length, the control circuit 80 may compute a desired ATP interval as a portion of the VT cycle length. However, microprocessor of the control circuit 80 may determine a leading, extended ATP interval that is longer than the desired ATP interval to control the timing of the leading ATP pulse. The microprocessor may load the extended ATP interval and the desired ATP interval in the pacer timing and control circuitry for controlling the timing of each pulse in the ATP sequence. For example one timer or counter of the pacer timing and control circuit may be set to the extended ATP interval for controlling the timing of the leading ATP pulse of an ATP sequence delivered by therapy delivery circuit 84. One or more timers may then be set to the desired ATP interval for controlling subsequent ATP pulses following the leading pulse of the ATP sequence. The leading, extended ATP interval may be determined by the microprocessor as being at least a predetermined interval longer than the desired ATP interval. This extended leading ATP interval promotes a high likelihood of capturing the myocardium when an the ATP sequence is delivered by an extra-cardiovascular pacing electrode vector and a time difference exists between the time that an R-wave is sensed by sensing circuit 86 and the time that a propagating depolarization associated with the sensed R-wave arrives at a capture site of the myocardium.

In the event that higher voltage cardioversion or defibrillation pulses are required, the control circuit microprocessor activates cardioversion and defibrillation control circuitry included in control circuit 80 to initiate charging of the high voltage capacitors of via a charging circuit, both included in therapy delivery circuit 84, under the control of a high voltage charging control line. The voltage on the high voltage capacitors is monitored via a voltage capacitor line, which is passed to control circuit 80. When the voltage reaches a predetermined value set by the microprocessor of control circuit 80, a logic signal is generated on a capacitor full line passed to therapy delivery circuit 84, terminating charging. The defibrillation or cardioversion pulse is delivered to the heart under the control of the pacer timing and control circuitry by an output circuit of therapy delivery circuit 84 via a control bus. The output circuit determines the electrodes used for delivering the cardioversion or defibrillation pulse and the pulse wave shape. Therapy delivery and control circuitry generally disclosed in any of the above-incorporated patents may be implemented in ICD 14.

Control parameters utilized by control circuit 80 for detecting cardiac rhythms and controlling therapy delivery may be programmed into memory 82 via telemetry circuit 88. Telemetry circuit 88 includes a transceiver and antenna for communicating with external device 40 (shown in FIG. 1A) using RF communication as described above. Under the control of control circuit 80, telemetry circuit 88 may receive downlink telemetry from and send uplink telemetry to external device 40. In some cases, telemetry circuit 88 may be used to transmit and receive communication signals to/from another medical device implanted in patient 12.

Figure 5:
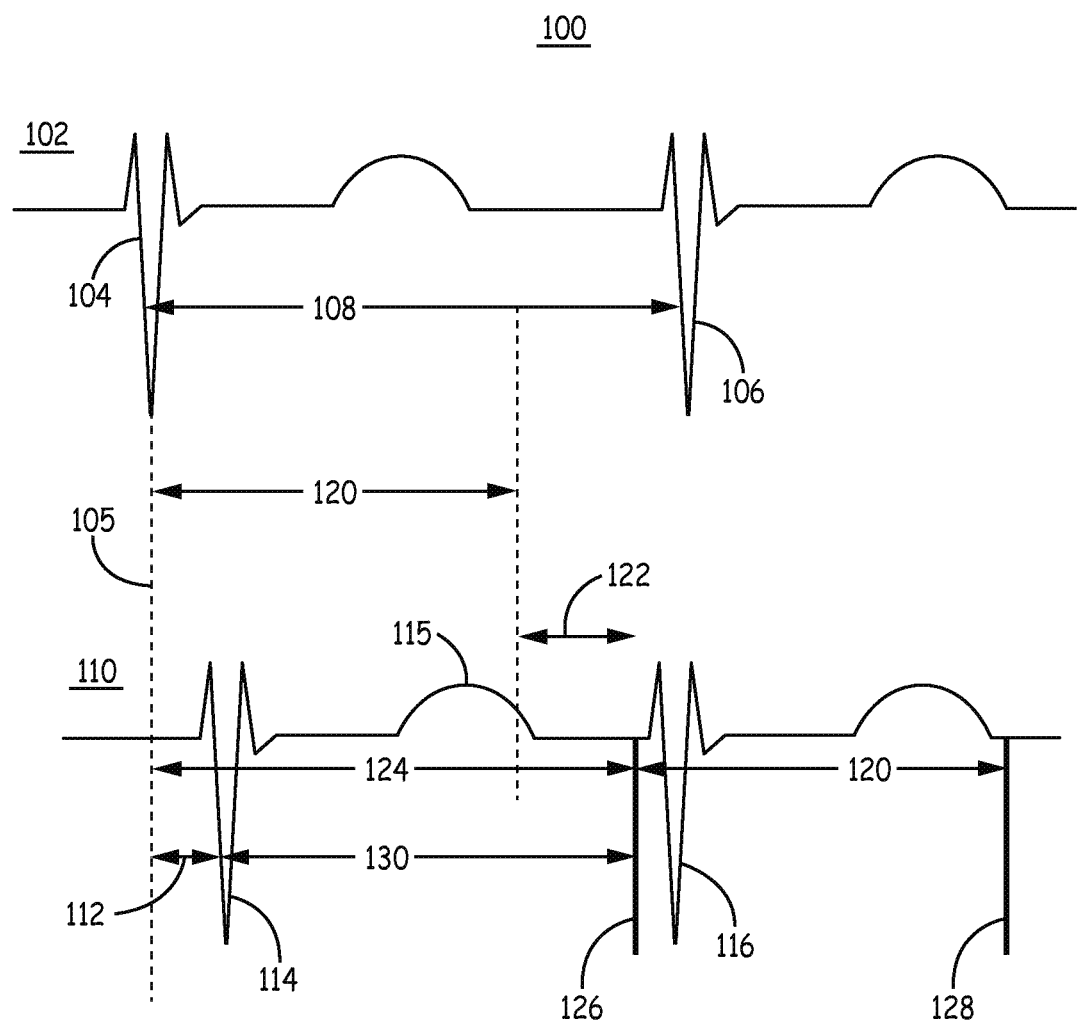
FIG. 5 is a diagram of an ECG signal that may be acquired using an extra-cardiovascular sensing electrode vector and an ECG signal representative of a cardiac electrical signal occurring at an effective capture site of an extra-cardiovascular pacing electrode vector.

FIG. 5 is a diagram 100 of an ECG signal 102 that may be acquired by sensing circuit 85 using an extra-cardiovascular sensing electrode vector and an ECG signal 110 representative of cardiac electrical signals occurring at an effective capture site of an extra-cardiovascular pacing electrode vector. ECG signal 102 includes an R-wave 104 that is sensed by electrical sensing circuit 86 at time 105. The next intrinsic R-wave 106 is shown to occur at a VT interval 108. An ATP interval 120 may be calculated by control circuit 80 based on the VT interval 108, e.g., as 80 percent or other percentage of the VT interval.

ECG signal 110 representative of cardiac electrical signals occurring at the capture site includes an R-wave 114 that occurs at a time interval 112 after the R-wave 104 is sensed by electrical sensing circuit 86. A pacing pulse delivered at the calculated ATP interval 120 from an R-wave sensed event signal produced by electrical sensing circuit 86 could occur during the myocardial refractory period at the capture site which includes the repolarization phase represented by T-wave 115. If the leading ATP pulse is delivered during the myocardial refractory period, the ATP pulse would likely fail to capture the myocardium. Subsequent ATP pulses would also likely arrive during the refractory period on subsequent cardiac cycles when the VT cycle length remains relatively stable and the leading ATP pulse fails to capture, such that all of the ATP pulses may fail to capture the heart and successfully terminate the VT.

The leading pacing pulse 126 of an ATP sequence delivered by extra-cardiovascular electrodes is delivered at an extended ATP interval 124 from the R-wave sensed event signal corresponding to sensed R-wave 104. The extended ATP interval 124 may be set to the VT cycle length 108 in some examples. The leading ATP pulse 126 may arrive just prior to or during the local depolarization at the capture site as represented by R-wave 116 and may or may not capture the heart. The next pacing pulse 128 of the ATP sequence, however, is delivered at the ATP interval 120 after leading pulse 126 and is expected to be outside of the refractory period that follows the preceding R-wave 116. The extended ATP interval 124 may alternatively be set to a predetermined short interval less than the VT cycle length 108, e.g., 10 ms less than the VT cycle length, or a higher percentage of the VT cycle length, e.g., 90 to 95% of the VT cycle length, compared to the relatively lower percentage used to calculate the ATP interval 120, e.g., 80 to 85% of the VT cycle length. Subsequent ATP pulses following the leading pulse 126 are delivered according to a desired ATP regime, e.g., burst, ramp, burst plus ramp, or other desired ATP sequence. Numerous patents describe ATP regimes that may be used for controlling the subsequent pulses of the ATP sequence, including U.S. Pat. No. 5,458,619 (Olson) and U.S. Pat. No. 6,167,308 (DeGroot), both incorporated herein by reference their entirety.

In other examples, in response to detecting VT, control circuit 80 may enable electrical sensing circuit 86 to acquire a cardiac electrical signal using one or both of the electrodes (cathode and/or anode) included in the pacing electrode vector that is used for delivering ATP. For example, the pacing electrode vector cathode may be used with the pacing electrode vector anode or another selected electrode or ICD housing 15 for sensing cardiac electrical signal 110 prior to delivery of the leading ATP pulse 126. The time interval 112, also referred to herein as the "time difference interval" or merely "difference interval," may be determined by control circuit 80 as the interval from the time that R-wave 104 is sensed by electrical sensing circuit 86 to a threshold crossing of R-wave 114, a maximum dV/dt of R-wave 114, a maximum rectified peak amplitude of R-wave 114, or other fiducial point of R-wave 114 acquired using at least one electrode of the pacing electrode vector.

Control circuit 80 may determine the extended ATP interval 120 used to control the timing of leading ATP pulse 126 by adding the difference interval 112 to the ATP interval 120 that is determined based on the VT cycle length 108. Alternatively, an ATP extension interval 122 may be determined that is longer than the difference interval 112 by adding a predetermined fixed interval or percentage of the difference interval 112 to the difference interval 112. ATP extension interval 122 may be added to the calculated ATP interval 120 for controlling delivery of the leading ATP pulse 126 at the extended ATP interval 124. The next ATP pulse 128 may be delivered at the determined ATP interval 120. Subsequent ATP pulses of the ATP sequence are delivered at the ATP interval 120 or according to a desired ATP regime. It is recognized that the various time intervals represented in FIG. 5, e.g., VT cycle length 108, the calculated ATP interval 120, the difference interval 112, the extension interval 122, and the extended ATP interval 124 may be determined by a microprocessor included in control circuit 80 using cardiac event signals received from sensing circuit 86 over multiple cardiac cycles.

Figure 6:
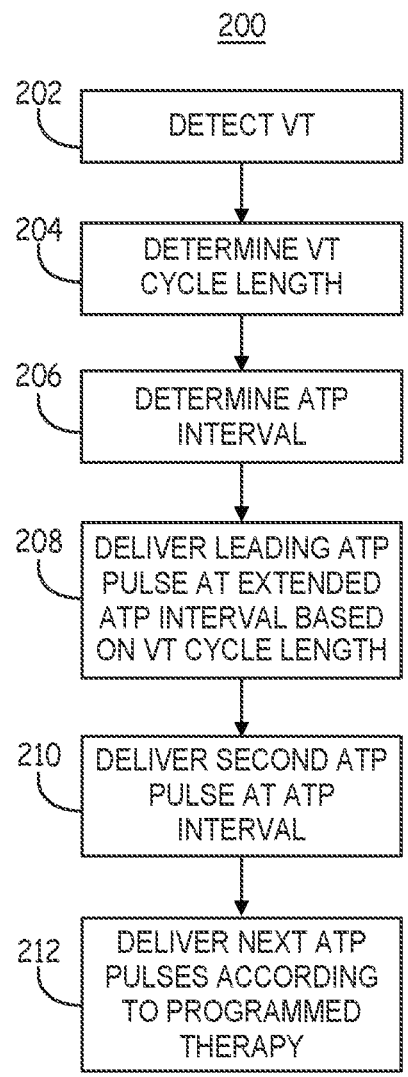
FIG. 6 is a flow chart of a method for delivering ATP by an extra-cardiovascular ICD system according to one example.

FIG. 6 is a flow chart 200 of a method for delivering ATP by an extra-cardiovascular ICD system according to one example. At block 202, ICD 14 detects VT according to an implemented tachyarrhythmia detection algorithm. VT is detected from the cardiac electrical signal received from one or more sensing electrode vector, e.g., between electrodes 28 and 30 shown in FIGS. 1A-3 or any of the sensing electrode vectors described above. At block 204, control circuit 80 determines the VT cycle length. The VT cycle length, e.g., VT cycle length 108 of FIG. 5, may be determined based on intervals between R-wave sensed event signals received from electrical sensing circuit 86. The VT cycle length determined by control circuit 80 is determined based on the cardiac electrical signal(s) acquired using the sensing electrode vector(s).

At block 206, the control circuit 80 determines a desired ATP interval based on the VT cycle length. The desired ATP interval may be a predetermined percentage of the VT cycle length, for example 80%, 85% or 90% of the VT cycle length. Alternatively, the desired ATP interval may be a predetermined amount of time less than the VT cycle length, e.g., 20 to 50 ms less than the VT cycle length. At block 208, control circuit 80 enables therapy delivery circuit 84 to deliver the leading ATP pulse at an extended ATP interval that is longer than the desired ATP interval. In one example, the leading ATP pulse is delivered at the VT cycle length at block 208. In another example, the leading ATP pulse is delivered at an interval slightly shorter than the VT cycle length, e.g., 10 ms shorter, but longer than the desired ATP interval determined at block 206.

The leading ATP pulse is synchronized to an R-wave sensed by electrical sensing circuit 86 using the sensing electrode vector. As illustrated in FIG. 5, the R-wave 104 may be sensed at time 105. Control circuit 80 may start the leading ATP interval 124 set equal to the VT cycle length 108 or to an interval that is slightly shorter than the VT cycle length but longer than the desired ATP interval 120. Upon expiration of the leading ATP interval 124, the leading ATP pulse 126 is delivered.

The leading ATP pulse may or may not capture the heart at the capture site depending on its timing relative to the next intrinsic depolarization occurring at the capture site. Referring again to FIG. 5, if the difference interval 112 between the time 105 at which R-wave 104 is sensed from a sensing electrode vector is negligible, such that the associated depolarization at the capture site occurs substantially at the same time as the sensed R-wave, the leading ATP pulse 126 may not capture at the capture site or a fusion beat may occur. A fusion beat occurs when some myocardial cells are depolarized by the delivered pacing pulse and others are depolarized by the propagating intrinsic depolarization wavefront.

Whether capture, fusion or non-capture occurs at the capture site in response to the leading pulse 126, the next ATP pulse 128 is properly timed to capture the myocardium at the capture site, outside the physiological refractory period and before the next intrinsic depolarization at the capture site. In this example of the difference interval 112 being negligible, the leading ATP pulse 126 could be delivered at the desired ATP interval 120 and successfully capture the myocardium at the capture site outside the physiological refractory period. Delivering the leading ATP pulse 126 at the extended ATP interval 124, however, promotes a high likelihood of all subsequent ATP pulses being outside physiological refractory without knowing whether difference interval 112 is negligible or not. In other words, control circuit 80 is not required to determine difference interval 112 in the method of flow chart 200.

When the difference interval 112 between the time 105 that R-wave 104 is sensed and when the depolarization at the capture site actually occurs is clinically significant, the leading ATP pulse 126 set to the VT cycle length will occur earlier than the next intrinsic depolarization at the capture site. As a result the leading ATP pulse 126 will capture the myocardium at the capture site and is likely to be outside the refractory period that follows the preceding intrinsic depolarization at the capture site. The next ATP pulse 128 delivered at the desired ATP cycle length is appropriately timed outside the refractory period following the pacing-evoked depolarization at the capture site and is at the intended, desired ATP interval 120. By delivering the leading pulse 126 at the VT cycle length or slightly shorter than the VT cycle length but extended from the desired ATP interval 120, the next ATP pulse 128 and all subsequent ATP pulses (not shown in FIG. 5) are expected to be appropriately timed for capturing the myocardium at the capture site outside of physiological refractory regardless of the difference interval 112.

Returning to the flow chart 200 of FIG. 6 with continued reference to FIG. 5, the next ATP pulse 128 is delivered at block 210 at the desired ATP interval 120 following the leading ATP pulse. At block 212, all subsequent ATP pulses are delivered according to a programmed ATP sequence. In one example, a sequence of 8 to 12 pulses are delivered at the desired ATP interval 120 with the exception of the leading pulse being delivered at the extended interval. However, the ATP sequence may include less than 8 pulses or more than 12 pulses in other instances. When the leading ATP pulse is delivered at the extended interval 124, the sequence may be extended by one pulse to ensure that a minimum desired number of ATP pulses capture the heart. For example, if the programmed ATP sequence is 8 pulses, the total number of pulses may be 9 including the leading pulse. Control circuit 80 determines if the ATP therapy successfully terminates the VT and responds with additional therapies as needed if the VT is re-detected or if VF is detected after ATP is complete.

Figure 7:
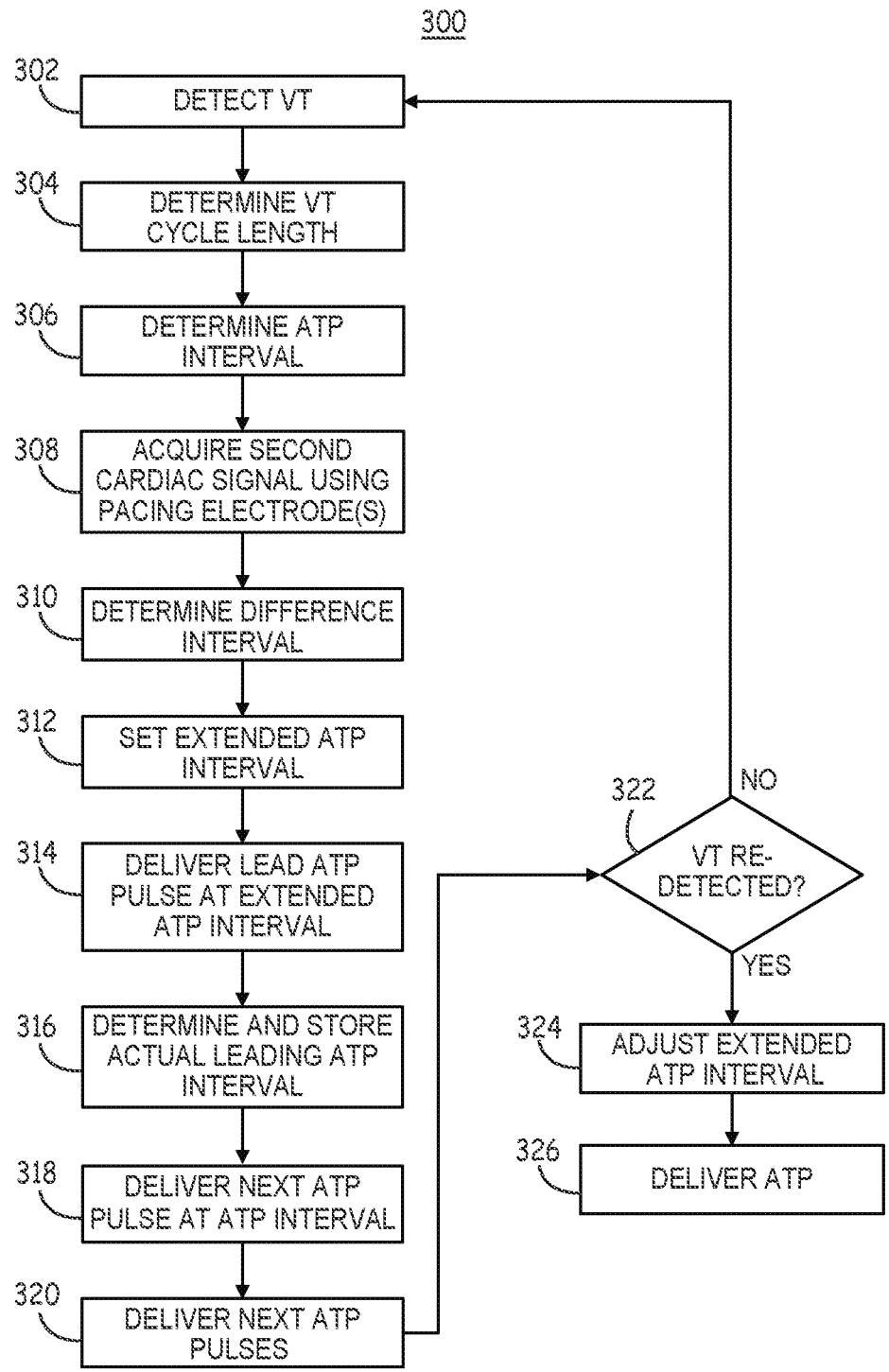
FIG. 7 is a flow chart of a method for delivering ATP by an extra-cardiovascular ICD system according to another example.

FIG. 7 is a flow chart 300 of a method for delivering ATP by an extra-cardiovascular ICD system according to another example. At block 302, the ICD 14 detects VT according to an implemented detection algorithm. The control circuit 80 determines the VT cycle length as described previously, e.g., from RR intervals between R-wave sensed event signals produced by the electrical sensing circuit 86. The VT cycle length is determined from a cardiac electrical signal acquired using a sensing electrode vector. At block 306, control circuit 80 determines a desired ATP interval based on the VT cycle length as described above in conjunction with FIGS. 5 and 6.

In response to detecting VT, control circuit 80 enables electrical sensing circuit 86 to acquire a cardiac electrical signal at block 308 using a second sensing electrode vector that is the same as the pacing electrode vector that is employed for delivering ATP. In other examples, the second cardiac electrical signal acquired at block 308 is acquired using a second sensing electrode vector that includes at least one of the electrodes used in the pacing electrode vector, e.g., at least the pacing cathode or at least the pacing anode. In order to determine a reliable estimate of the time interval between an R-wave sensed event signal from the first sensing electrode vector and a depolarization at the capture site, the second cardiac electrical signal acquired at block 308 may be obtained using at least the pacing cathode electrode in one example. The pacing electrode vector and the first sensing electrode vector are different vectors. The pacing electrode vector and the second sensing electrode vector may be the same vectors or have at least one electrode in common.

Control circuit 80 determines the difference interval 112 (FIG. 5) at block 310. The difference interval 112 may be determined by identifying a fiducial point of an R-wave of the second cardiac electrical signal received by the second sensing electrode vector, using one or both electrodes included in the pacing electrode vector. As described above, the fiducial point may be, without limitation, a threshold crossing, a maximum peak amplitude of the rectified cardiac electrical signal, or a maximum dV/dt. The difference interval 112 may be determined as the time interval from an R-wave sensed event signal produced using the first sensing electrode vector and the fiducial point determined from the second sensing electrode vector. In other examples, an analogous fiducial point of the R-wave of the first sensing electrode vector signal may be determined and the difference interval 112 is determined between the fiducial point of the R-wave from the first sensing electrode vector signal and the analogous fiducial point of the R-wave from the second sensing electrode vector signal, which may be the pacing vector or includes at least one electrode of the pacing electrode vector used to deliver ATP.

The control circuit 80 determines and sets an extended ATP interval at block 312. The extended ATP interval is determined based on the difference interval determined at block 310 and the VT cycle length determined at block 304 and/or the desired ATP interval determined at block 306. For example, the extended ATP interval may be set to the desired ATP interval determined at block 306 plus the determined difference interval. The extended ATP interval is started by the pacer timing and control circuitry of control circuit 80 upon sensing an R-wave from the first sensing electrode vector, e.g., upon receiving an R-wave sensed event signal from sensing circuit 86. The extended ATP interval may be set to an interval that is at least the desired ATP interval plus the difference interval up to the VT cycle length plus the difference interval. In this way, the leading ATP pulse has a high likelihood of being delivered outside the myocardial refractory period at the capture site.

The leading ATP pulse is delivered by the therapy delivery circuit 84 upon expiration of the extended ATP interval at block 314. At block 316, an actual leading ATP interval may be stored for use in ATP feedback and analysis algorithms. The actual leading ATP interval is based on the time of the most recent intrinsic depolarization at the myocardium as estimated by the R-wave fiducial point of the second cardiac electrical signal acquired by the second sensing electrode vector used to determine the difference interval 112. The actual leading ATP interval is the time from the fiducial point to the leading ATP pulse, e.g., interval 130 in FIG. 5. This actual leading ATP interval may be used when evaluating the effectiveness of the ATP therapy in terminating the VT.

At block 318, the second ATP pulse (following the leading ATP pulse) is delivered at the desired ATP interval determined at block 306 based on the detected VT cycle length. All remaining ATP pulses are delivered at block 320 according to the programmed ATP therapy regime. For example, a sequence of 8 to 12 pulses may be delivered at the ATP interval determined at block 306. In other examples, a ramp sequence of ATP pulses may be delivered in which each successive ATP pulse interval is shorter than the immediately preceding ATP pulse interval. It is recognized that numerous ATP sequences that define the number and intervals of ATP pulses following the leading pulse may be used according to the ATP therapies implemented in the ICD 14.

In some examples, the stored, actual leading ATP interval may be used to adjust the extended ATP interval for subsequent ATP sequences if the ATP fails to terminate the detected tachycardia. As shown in FIG. 7, if VT is not redetected at block 322, the ICD may return to block 302 to wait for the next VT detection. If VT is redetected, the extended ATP interval is adjusted at block 324 so that it is different than the extended ATP interval used to deliver the first ATP sequence. The adjusted, extended ATP interval may be set to be equal to or less than the VT cycle length but greater than the VT cycle length minus the time difference interval determined at block 310. The adjusted, extended ATP interval may be made longer than or shorter than the first extended ATP interval, which may depend on the actual leading ATP interval determined at block 316. For example, if the actual leading ATP interval is found to be shorter than the ATP interval determined at block 306 or shorter than the VT cycle length less the time difference interval, the adjusted extended ATP interval may be increased. If the actual leading ATP interval is determined to be longer than the VT cycle length, the extended ATP interval may be shortened.

At block 326, control circuit 80 controls therapy delivery circuit 84 to deliver a second sequence of ATP pulses having a leading pulse delivered at the adjusted, extended ATP interval following a cardiac event sensed by the electrical sensing circuit 86 from the sensing electrode vector and deliver the next ATP pulse at the desire ATP interval, determined at block 306, following the leading pulse. The example shown in FIG. 7 includes delivery of two ATP sequences in an attempt to terminate the VT. It is recognized that more than two ATP sequences may be delivered to terminate the VT. It is understood that if a maximum number of ATP sequences are delivered without terminating the VT, a cardioversion/defibrillation shock may be delivered by ICD 14.

Figure 8:
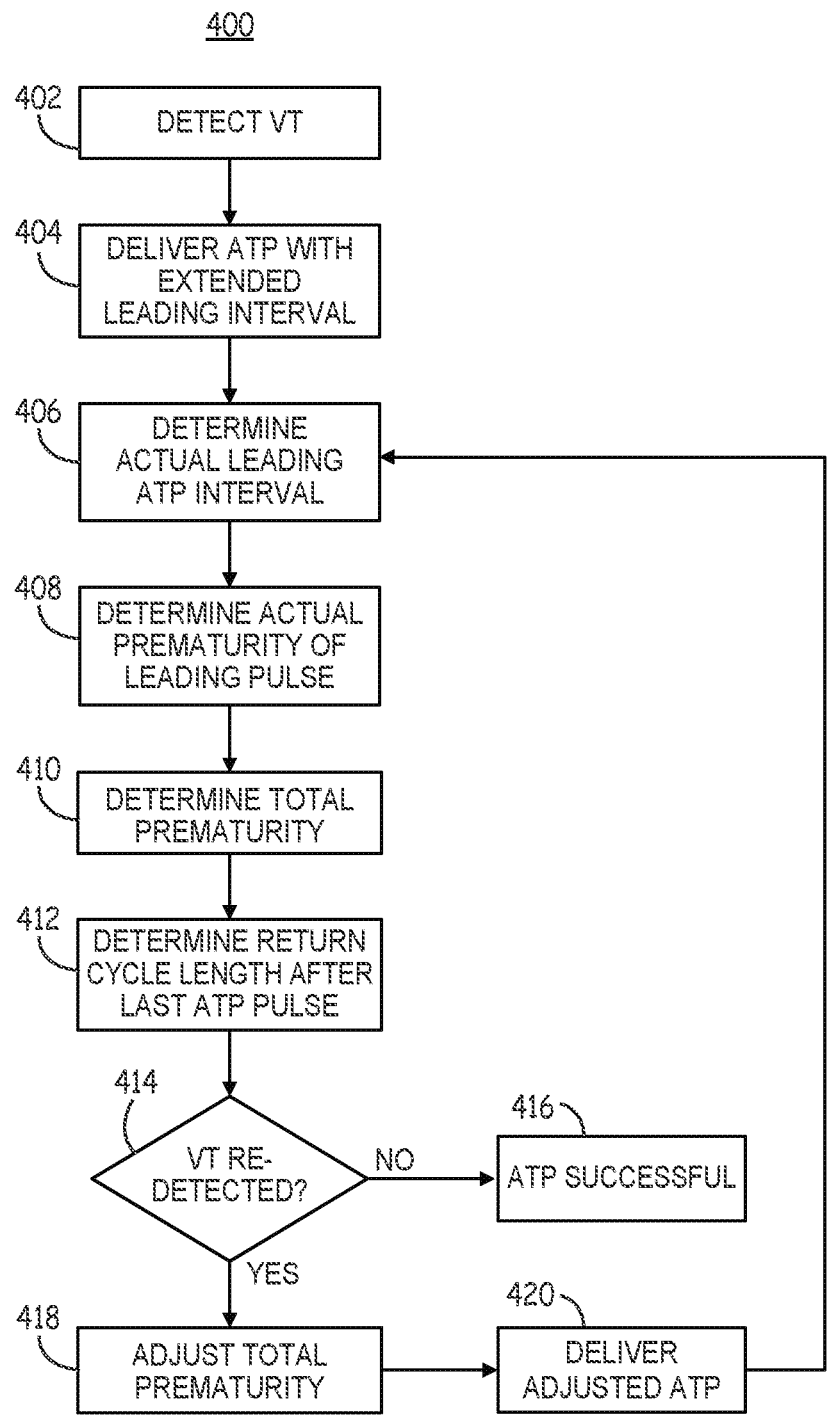
FIG. 8 is a flow chart of a method for controlling ATP delivered by an extra-cardiovascular ICD system according to another example.

FIG. 8 is a flow chart 400 of a method for controlling ATP delivered by an extra-cardiovascular ICD system according to another example. At block 402, ICD 14 detects VT and delivers ATP at block 404 including a leading ATP pulse delivered at an extended ATP interval that is set based on determining the VT cycle length and the difference interval as described in conjunction with the flow chart 300 of FIG. 7. The actual ATP interval of the leading pulse is determined as the difference between the difference interval and the extended ATP interval at block 406. For example, as shown in FIG. 5, the actual leading ATP interval 130 is the extended ATP interval 124 less the difference interval 112.

At block 408, the actual prematurity of the leading pulse is determined by control circuit 80. The prematurity of an individual ATP pulse is generally the difference between the ATP interval used to control the time that the ATP pulse is delivered and the VT cycle length. However, in the case of the extra-cardiovascular ICD system 10, the actual prematurity of the leading pulse of a series of ATP pulses will depend on the difference interval 112 (FIG. 5). As such, the actual prematurity of the leading pulse 126 shown in FIG. 5 may be determined as the VT cycle length 108 less the extended ATP interval 124 plus the difference interval 112.

If an N pulse ATP sequence is delivered, all remaining ATP pulses are delivered at the determined desired ATP interval, e.g. ATP interval 120 shown in FIG. 5. The individual prematurity of each of the remaining ATP pulses (i.e., the second through N pulses) is the VT cycle length 108 less the ATP interval 120. Control circuit 80 may be configured to determine the total prematurity of the ATP therapy at block 410 as the sum of the individual prematurities of all pulses in the ATP sequence. In one example, if the VT cycle length is 380 ms, the ATP interval 120 may be determined to be 305 ms (approximately 80% of the VT cycle length). If a sequence of 8 pulses are delivered, the second through eighth pulses each have an individual prematurity of 75 ms. If the extended ATP interval 124 is set to the VT cycle length less 10 ms, or 370 ms, and the difference interval is determined to be 20 ms, the individual prematurity of the leading pulse is 10 ms (380 ms minus 370 ms plus 20 ms). The total prematurity of the 8-pulse sequence is approximately 535 ms (10 ms prematurity of the leading pulse plus 7 times the 75 ms individual prematurity of the remaining seven pulses).

At block 412, the control circuit may determine the return cycle length after the last ATP pulse as the time from the last ATP pulse to the earliest occurring R-wave after the last ATP pulse. If VT is not redetected after ATP, as determined at block 414, the ATP sequence was successful as indicated at block 416. If VT is redetected at block 414, however, the control circuit 80 may determine a new ATP sequence having an adjusted total prematurity based on the total prematurity of the delivered ATP and the return cycle length determined at block 412. The total prematurity may need to be increased in order to successfully terminate the VT. Techniques for analyzing the response to an ATP therapy and adjusting the total prematurity in response to redetecting VT are generally disclosed in U.S. Pat. No. 8,706,221 (Belk, et al.), incorporated herein by reference in its entirety.

The total prematurity may be increased at block 418 by increasing the individual prematurity of one or more pulses in an ATP sequence and/or increasing the total number of pulses in the ATP sequence. In one example, the individual prematurity of the leading ATP pulse is increased by shortening the extended ATP interval to a minimum leading ATP interval that is not less than the desired ATP interval 120 plus the difference interval 112. The adjusted ATP sequence having an increased total prematurity is delivered at block 420. This process may be repeated by returning to block 406 to allow multiple ATP attempts using the actual prematurity of the leading ATP pulse in determining the total prematurity of the ATP sequence for feedback in making ATP therapy adjustments. While not explicitly shown in FIG. 8, it is recognized that a maximum number of ATP attempts may be made prior to delivering a shock therapy to terminate a VT rhythm that is not successfully terminated by ATP therapy. For example, the total prematurity may be adjusted at block 418 after the first ATP attempt, and the adjusted ATP sequence having the increased total prematurity may be delivered at block 418 without returning to block 406. If VT is re-detected after the second ATP attempt, control circuit 80 may control therapy circuit 84 to deliver a shock therapy to terminate the VT. It is further recognized that if the VT accelerates such that VF is detected after any ATP attempt, a shock therapy may be delivered as needed to terminate the tachyarrhythmia.

Thus, a method and apparatus for delivering anti-tachycardia pacing pulses using extra-cardiovascular electrodes have been presented in the foregoing description with reference to specific embodiments. In other examples, various methods described herein may include steps performed in a different order or combination than the illustrative examples shown and described herein. It is appreciated that various modifications to the referenced embodiments may be made without departing from the scope of the disclosure and the following claims.

The invention claimed is:

1. A medical device comprising:
 a sensing circuit configured to:
  receive a first cardiac electrical signal via a first electrode pair;
  sense cardiac events each associated with a myocardial depolarization from the first cardiac electrical signal;
  receive a second cardiac electrical signal via a second electrode pair different than the first electrode pair;
 a control circuit configured to:
  determine a difference time interval between a cardiac event sensed from the first cardiac electrical signal and a fiducial point of the second cardiac electrical signal;
  detect tachycardia from the first cardiac electrical signal; and
  determine a first anti-tachycardia pacing (ATP) interval based on at least the difference time interval; and
 a therapy delivery circuit configured to, in response to the control circuit detecting the tachycardia, deliver an ATP therapy by delivering a first leading ATP pulse at the first ATP interval from a cardiac event sensed by the sensing circuit from the first cardiac electrical signal after the control circuit detects the tachycardia.

2. The medical device of claim 1 wherein the control circuit is further configured to:
 determine a tachycardia cycle length from the first cardiac electrical signal; and
 determine the first ATP interval based on the tachycardia cycle length and the difference time interval.

3. The medical device of claim 1 wherein:
 the control circuit is further configured to:
  determine a tachycardia cycle length from the first cardiac electrical signal; and
  determine a second ATP interval based on the determined tachycardia cycle length; and the therapy delivery circuit is further configured to deliver the ATP therapy by delivering a second ATP pulse at the second ATP interval from the first leading ATP pulse.

4. The medical device of claim 3 wherein the control circuit is further configured to:
determine the first ATP interval based on a first percentage of the tachycardia cycle length and the difference time interval; and
determine the second ATP interval based on a second percentage of the tachycardia cycle length.

5. The medical device of claim 1 further comprising a memory, wherein:
the control circuit is further configured to:
determine from the second cardiac electrical signal an actual leading time interval to the first leading ATP pulse; and
store the actual leading time interval in the memory.

6. The medical device of claim 1 further comprising a memory, wherein:
the control circuit is further configured to:
determine a tachycardia cycle length from the first cardiac electrical signal;
determine an actual prematurity of the first leading ATP pulse based on at least the tachycardia cycle length and the first ATP interval;
determine a first total prematurity of the ATP therapy including the actual prematurity of the first leading pulse; and
store the first total prematurity in the memory.

7. The medical device of claim 6 wherein:
the control circuit is further configured to redetect the tachycardia after the therapy delivery circuit delivers the ATP therapy; and
the therapy delivery circuit is further configured to deliver the ATP therapy having a second total prematurity that is greater than the first total prematurity of the ATP therapy after the control circuit redetects the tachycardia.

8. The medical device of claim 1 wherein the therapy delivery circuit is further configured to deliver the ATP therapy via the second electrode pair.

9. The medical device of claim 1 wherein the therapy delivery circuit is further configured to deliver the ATP therapy via a third electrode pair, the third electrode pair having a common electrode with the second electrode pair.

10. The medical device of claim 1 wherein the control circuit is further configured to determine the fiducial point of the second cardiac electrical signal by determining at least one of:
a threshold crossing;
a maximum slope; or
a maximum peak.

11. A method comprising:
receiving a first cardiac electrical signal via a first electrode pair;
sensing cardiac events each associated with a myocardial depolarization from the first cardiac electrical signal;
receiving a second cardiac electrical signal via a second electrode pair different than the first electrode pair;
determining a difference time interval between a cardiac event sensed from the first cardiac electrical signal and a fiducial point of the second cardiac electrical signal;
detecting tachycardia from the first cardiac electrical signal;
determining a first anti-tachycardia pacing (ATP) interval based on at least the difference time interval; and in response to detecting the tachycardia, delivering an ATP therapy by delivering a first leading ATP pulse at the first ATP interval from a cardiac event sensed by the sensing circuit from the first cardiac electrical signal after detecting the tachycardia.

12. The method of claim 11 further comprising:
determining a tachycardia cycle length from the first cardiac electrical signal; and
determining the first ATP interval based on the tachycardia cycle length and the difference time interval.

13. The method of claim 11 further comprising:
determining a tachycardia cycle length from the first cardiac electrical signal; and
determining a second ATP interval based on the determined tachycardia cycle length; and
the therapy delivery circuit is further configured to deliver the ATP therapy by delivering a second ATP pulse at the second ATP interval from the first leading ATP pulse.

14. The method of claim 13 further comprising:
determining the first ATP interval based on a first percentage of the tachycardia cycle length and the difference time interval; and
determining the second ATP interval based on a second percentage of the tachycardia cycle length.

15. The method of claim 11 further comprising:
determining from the second cardiac electrical signal an actual leading time interval to the first leading ATP pulse; and
storing the actual leading time interval in a memory of a medical device.

16. The method of claim 11 further comprising:
determining a tachycardia cycle length from the first cardiac electrical signal;
determining an actual prematurity of the first leading ATP pulse based on at least the tachycardia cycle length and the first ATP interval; and
determining a first total prematurity of the ATP therapy including the actual prematurity of the first leading pulse.

17. The method of claim 16 further comprising:
redetecting the tachycardia after the ATP therapy is delivered; and
after redetecting the tachycardia, delivering the ATP therapy having a second total prematurity that is greater than the first total prematurity.

18. The method of claim 11 further comprising delivering the ATP therapy via the second electrode pair.

19. The method of claim 11 further comprising delivering the ATP therapy via a third electrode pair, the third electrode pair having a common electrode with the second electrode pair.

20. The method of claim 11 further comprising determining the fiducial point of the second cardiac electrical signal by determining at least one of:
a threshold crossing;
a maximum slope; or
a maximum peak.

21. A non-transitory computer readable medium storing a set of instructions which, when executed by a control circuit of a medical device, cause the medical device to:
receive a first cardiac electrical signal via a first electrode pair;
sense cardiac events each associated with a myocardial depolarization from the first cardiac electrical signal;
receive a second cardiac electrical signal via a second electrode pair different than the first electrode pair;

determine a difference time interval between a cardiac event sensed from the first cardiac electrical signal and a fiducial point of the second cardiac electrical signal;

detect tachycardia from the first cardiac electrical signal;

determine an anti-tachycardia pacing (ATP) interval based on at least the difference time interval; and in response to detecting the tachycardia, delivering an ATP therapy by delivering a first leading ATP pulse of the ATP therapy at the ATP interval from a cardiac event sensed by the sensing circuit from the first cardiac electrical signal after detecting the tachycardia.

* * * * *